United States Patent
Ishiyama et al.

(10) Patent No.: US 7,163,921 B1
(45) Date of Patent: Jan. 16, 2007

(54) PEPTIDE DERIVATIVES AND MEDICINAL COMPOSITIONS

(75) Inventors: Kouichi Ishiyama, Tsukuba (JP); Tomohiro Terada, Isukuba (JP); Tatsuya Oyama, Nagaokakyo (JP); Tadaaki Ohgi, Tsuchiura (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 124 days.

(21) Appl. No.: 10/257,238

(22) PCT Filed: Apr. 16, 2001

(86) PCT No.: PCT/JP01/03220

§ 371 (c)(1), (2), (4) Date: Oct. 9, 2002

(87) PCT Pub. No.: WO01/79263

PCT Pub. Date: Oct. 25, 2001

(30) Foreign Application Priority Data

Apr. 14, 2000  (JP) .............................. 2000-114248
Dec. 27, 2000  (JP) .............................. 2000-396605

(51) Int. Cl.
*A61K 38/07* (2006.01)
*A61K 38/05* (2006.01)
*A61K 38/06* (2006.01)
*C07K 5/08* (2006.01)
*C07K 7/04* (2006.01)

(52) U.S. Cl. .............................. 514/18; 514/2; 514/19; 514/20; 530/300; 530/330; 530/331

(58) Field of Classification Search .................... 514/2; 530/300; 540/1; 564/1, 11, 12, 153, 155, 564/159
See application file for complete search history.

(56) References Cited

U.S. PATENT DOCUMENTS 5,332,726 A  7/1994  Klein et al.
5,663,295 A  9/1997  Moreau et al. ............. 530/330
6,051,685 A  4/2000  Sakurada et al. ........... 530/331

FOREIGN PATENT DOCUMENTS

JP         7-5034845 A   4/1995
WO    WO 94/11018       5/1994
WO    WO 95/01371       1/1995

OTHER PUBLICATIONS

J Rosén, et al. A Human serine endopeptidase, purified with respect to activity against a peptide with phosphoserine in the P1' position, is apparently identical with prolyl endopeptidase. (1991) J. Biol. Chem. 266, 3827-3834.*

J Grehn, et al. Synthesis and cAMP dependent phosphorylation of Gva-Arg-Ala-Ser-NH-i-Bu. Pept. (1993) 1992, Proc. Eur. Pept. Symp., 22nd, Meeting Date, 1992, 798-799. Abstract only (56-57).*
Pheng, L.H., et al "[Nphe1]nociceptin-1(1-13)NH2 selectively antagonizes nociceptin effects in the rabbit isolated ileum", Apr. 7, 2000 European Journal of Pharmacology, vol. 397 (2/3), pp. 382-388 (6 pages).
Okada, Kazushi, et al., "Structure-activity studies on nociceptive peptides", 1999, Tampakushitsu Kakusan Koso, vol. 44 (9), pp. 1369-1377 (10 pages).
English Language translation of relevance of above cited document.
Supplementary European Search Report (01921846.0-PCT/JP0103220) Nippon Shinyaku Co., Ltd.

* cited by examiner

*Primary Examiner*—Anish Gupta
*Assistant Examiner*—Andrew D. Kosar
(74) *Attorney, Agent, or Firm*—Greenberg Traurig

(57) ABSTRACT

The present invention to novel nociceptin receptor agonists which are peptide derivatives represented by the following general formula (1):

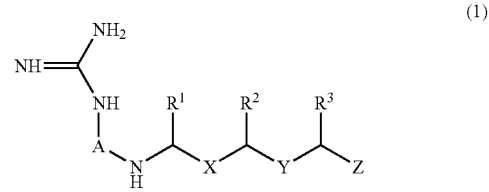

(in which A is alkylene, —CH$_2$)$_n$CO— or a group expressed by the following formula (2) or (3):

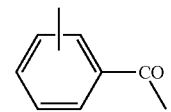

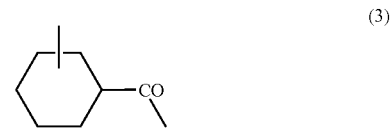

wherein n represents an integer of 1 to 8; X and Y are same or different and each represents —CONH— or —CH$_2$NH—; R$^1$, R$^2$ and R$^3$ are same or different and each represents alkyl, aryl or heteroaryl; Z represents —CON(R$^4$)R$^5$ or —CH$_2$N(R$^4$)R$^5$; R$^4$ and R$^5$ are same or different and each represents hydrogen, alkyl, aryl or heteroaryl) or a pharmaceutically acceptable salt thereof. A pharmaceutical composition according to the present invention is useful as a nociceptin receptor agonist.

5 Claims, 2 Drawing Sheets

Method [1]

SEQUENCE LISTING

<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: SYNTHETIC PEPTIDE N-terminal amino acid residue
      is substituted by guanidinoacyl, C-terminal amino acid residue is
      amide

<400> SEQUENCE: 1

Tyr Tyr Arg Trp
1

<210> SEQ ID NO 2
<211> LENGTH: 4
<212> TYPE: PRT
<213> ORGANISM: Artificial Sequence
<220> FEATURE:
<223> OTHER INFORMATION: SYNTHETIC PEPTIDE N-terminal amino acid residue
      is substituted by guanidinoalkyl, C-terminal amino acid residue is
      amide.

<400> SEQUENCE: 2

Tyr Tyr Arg Trp

```
<210> SEQ ID NO 3
<211> LENGTH: 4
<212> TYPE: PRT
<213> ORGANISM: Artificial Sequence
<220> FEATURE:
<223> OTHER INFORMATION: SYNTHETIC PEPTIDE N-terminal amino acid residue
      is substituted by guanidinoalkyl, C-terminal amino acid residue is
      amide

<400> SEQUENCE: 3

Ala Tyr Lys Trp
1

<210> SEQ ID NO 4
<211> LENGTH: 4
<212> TYPE: PRT
<213> ORGANISM: artificial Sequence
<220> FEATURE:
<223> OTHER INFORMATION: SYNTHETIC PEPTIDE N-terminal amino acid residue
      is substituted by guanidinoacyl, C-terminal amino acid residue is
      amide

<400> SEQUENCE: 4

Ala Tyr Lys Trp
1

<210> SEQ ID NO 5
<211> LENGTH: 4
<212> TYPE: PRT
<213> ORGANISM: artificial Sequence
<220> FEATURE:
<223> OTHER INFORMATION: SYNTHETIC PEPTIDE N-terminal amino acid residue
      is substituted by guanidinoalkyl, C-terminal amino acid residue is
      amide

<400> SEQUENCE: 5

Phe Tyr Lys Trp
1

<210> SEQ ID NO 6
<211> LENGTH: 4
<212> TYPE: PRT
<213> ORGANISM: artificial Sequence
<220> FEATURE:
<223> OTHER INFORMATION: SYNTHETIC PEPTIDE N-terminal amino acid residue
      is substituted by guanidinoacyl, C-terminal amino acid residue is
      amide

<400> SEQUENCE: 6

Phe Tyr Lys Trp
1

<210> SEQ ID NO 7
<211> LENGTH: 4
<212> TYPE: PRT
<213> ORGANISM: artificial Sequence
<220> FEATURE:
<223> OTHER INFORMATION: SYNTHETIC PEPTIDE N-terminal amino acid residue
      is substituted by guanidinoalkyl, C-terminal amino acid residue is
      amide

<400> SEQUENCE: 7

Gly Tyr Lys Trp
1

<210> SEQ ID NO 8
```

```
<211> LENGTH: 4
<212> TYPE: PRT
<213> ORGANISM: artificial Sequence
<220> FEATURE:
<223> OTHER INFORMATION: SYNTHETIC PEPTIDE N-terminal amino acid residue
      is substituted by guanidinoacyl, C-terminal amino acid residue is
      amide

<400> SEQUENCE: 8

Gly Tyr Lys Trp
1

<210> SEQ ID NO 9
<211> LENGTH: 4
<212> TYPE: PRT
<213> ORGANISM: artificial Sequence
<220> FEATURE:
<223> OTHER INFORMATION: SYNTHETIC PEPTIDE N-terminal amino acid residue
      is substituted by guanidinoalkyl, C-terminal amino acid residue is
      amide

<400> SEQUENCE: 9

Tyr Tyr Lys Trp
1

<210> SEQ ID NO 10
<211> LENGTH: 4
<212> TYPE: PRT
<213> ORGANISM: artificial Sequence
<220> FEATURE:
<223> OTHER INFORMATION: SYNTHETIC PEPTIDE N-terminal amino acid residue
      is substituted by guanidinoacyl, C-terminal amino acid residue is
      amide

<400> SEQUENCE: 10

Tyr Tyr Lys Trp
1

<210> SEQ ID NO 11
<211> LENGTH: 4
<212> TYPE: PRT
<213> ORGANISM: artificial Sequence
<220> FEATURE:
<223> OTHER INFORMATION: SYNTHETIC PEPTIDE N-terminal amino acid residue
      is substituted by guanidinoalkyl, C-terminal amino acid residue is
      amide

<400> SEQUENCE: 11

Tyr Tyr Lys Phe
1

<210> SEQ ID NO 12
<211> LENGTH: 4
<212> TYPE: PRT
<213> ORGANISM: artificial Sequence
<220> FEATURE:
<223> OTHER INFORMATION: SYNTHETIC PEPTIDE N-terminal amino acid residue
      is substituted by guanidinoacyl, C-terminal amino acid residue is
      amide

<400> SEQUENCE: 12

Tyr Tyr Lys Phe
1
```

PEPTIDE DERIVATIVES AND MEDICINAL COMPOSITIONS

TECHNICAL FIELD

The present invention relates to a novel peptide derivative useful as a pharmaceutical or a pharmaceutically acceptable salt thereof, and a pharmaceutical composition containing the same as an active ingredient.

BACKGROUND ART

There are used, as an analgesic, a narcotic analgesic (morphine and the like), a non-narcotic analgesic (aspirin, indomethacin and the like) and a narcotic-antagonistic analgesic (pentazocine and the like). A narcotic analgesic exerts its analgesic effect by inhibiting an algesic excitation transmission mainly in a central system. A non-narcotic analgesic exerts its analgesic effect by inhibiting the production of a dorologenic substance mainly in a peripheral system. A narcotic-antagonistic analgesic exerts its analgesic effect by a mechanism similar to that of a narcotic analgesic.

Nevertheless, there are no useful analgesics against a chronic pain which cannot be suppressed by a morphine, an allodynia associated with herpes zoster or a hyperalgesia, and an excellent analgesic has been still demanded.

Recently, an opioid receptor such as mu (μ), delta (δ) or kappa (κ) opioid receptor was identified, and a further novel subtype receptor, namely, nociceptin receptor (ORL-1) was identified while its intrinsic agonist nociceptin was also found. The nociceptin receptor (ORL-1) agonist is suggested to be effective in treating a neural inflammation, and this agonist is a highly effective analgesic which has less psychological side effects and causes less indulgence.

DISCLOSURE OF THE INVENTION

The present inventors searched for a compound having an effect on the nociceptin receptor (ORL-1) and finally found that a peptide derivative expressed by the following general formula (1) or a pharmaceutically acceptable salt is an agonist of the nociceptin receptor (ORL-1) and has a potent analgesic effect, thereby establishing the present invention. It was also found that a compound of the present invention is useful as an analgesic or as an anxiolytic agent.

A peptide derivative according to the present invention is expressed by general formula (1):

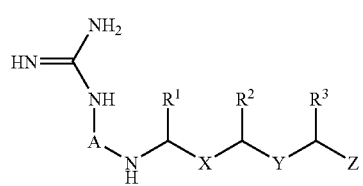

in which A is alkylene, —(CH$_2$)$_n$CO— or a group by formula (2) or (3):

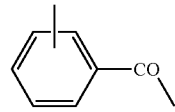

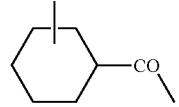

X and Y are same or different and each represents —CONH— or —CH$_2$NH—;

R$^1$, R$^2$ and R$^3$ are same or different and each represents alkyl, aryl or heteroaryl, such alkyl, aryl and heteroaryl being optionally substituted by 1 to 3 same or different substituents selected from a group consisting of halogen, nitro, hydroxy, carboxy, cyano, carbamoyl, alkyl, aryl (optionally substituted by hydroxy), heteroaryl (optionally substituted by hydroxy), alkenyl, alkynyl, alkoxycarbonyl, acyl, amino, monoalkylamino, dialkylamino, alkoxy, aryloxy, arylalkyloxy, alkylthio, arylalkylthio, heteroarylalkylthio, arylsulfonyl, alkylsulfonyl and guanidino;

Z represents —CON(R$^4$)R$^5$ or —CH$_2$N(R$^4$)R$^5$ wherein R$^4$ and R$^5$ are same or different and each represents hydrogen, alkyl, aryl or heteroaryl, such alkyl, aryl and heteroaryl being optionally substituted by 1 to 3 same or different substituents selected from a group consisting of halogen, nitro, hydroxy, carboxy, cyano, carbamoyl, alkyl, aryl (optionally substituted by hydroxy), heteroaryl (optionally substituted by hydroxy), alkenyl, alkynyl, alkoxycarbonyl, acyl, amino, monoalkylamino, dialkylamio, alkoxy, aryloxy, arylalkyloxy, alkylthio, arylalkylthio, heteroarylalkylthio, arylsulfonyl, alkylsulfonyl, guanidino, N-monoalkylcarbamoyl (alkyl is optionally substituted), N,N-dialkylcarbamoyl (alkyl is optionally substituted with halogen, nitro, hydroxy, carboxy, cyano, carbamoyl, alkyl and aryl) and hydroxymethyl (methyl is optionally substituted by halogen, nitro, hydroxy, carboxy, cyano, carbamoyl, alkyl and aryl).

In the present invention, examples of "alkyl" may include a group of a straight or branched chain having 1 to 6 carbon atoms such as methyl, ethyl, n-propyl, isopropyl, n-butyl, isobutyl, sec-butyl, tert-butyl, n-pentyl, isopentyl, neopentyl and n-hexyl.

In the present invention, examples of "aryl" may include a group having 6 to 12 carbon atoms such as phenyl and naphthyl.

In the present invention, examples of "heteroaryl" may include a 5 to 6-membered ring having 1 to 4 nitrogen, oxygen or sulfur atoms or a fused ring thereof with a benzene ring, such as pyrrolyl, furyl, thienyl, imidazolyl, pyrazolyl, pyridyl, indoryl, benzofuryl, benzoimidazolyl, benzothienyl, quinolyl and isoquinolyl.

In the present invention, examples of "halogen" may include fluorine, chlorine, bromine and iodine.

In the present invention, examples of "alkenyl" may include a group of a straight or branched chain having 2 to 3 carbon atoms such as vinyl, propenyl and isopropenyl.

In the present invention, examples of "alkynyl" may include a chain having 2 to 3 carbon atoms such as ethynyl and propargyl.

In the present invention, examples of each alkyl moiety in "alkoxycarbonyl", "monoalkylamino", "dialkylamino", "alkoxy", "arylalkyloxy", "alkylthio", "arylalkylthio", "heteroarylalkylthio", "alkylsulfonyl", "N-monoalkylcarbamoyl" and "N,N-dialkylcarbamoyl" may include the above described alkyl.

In the present invention, examples of each aryl moiety in "aryloxy", "arylalkyloxy", "arylalkylthio" and "arylsulfonyl" may include the above described aryl.

In the present invention, examples of each heteroaryl moiety in "heteroarylalkylthio" may include the above described heteroaryl.

Figure 1:
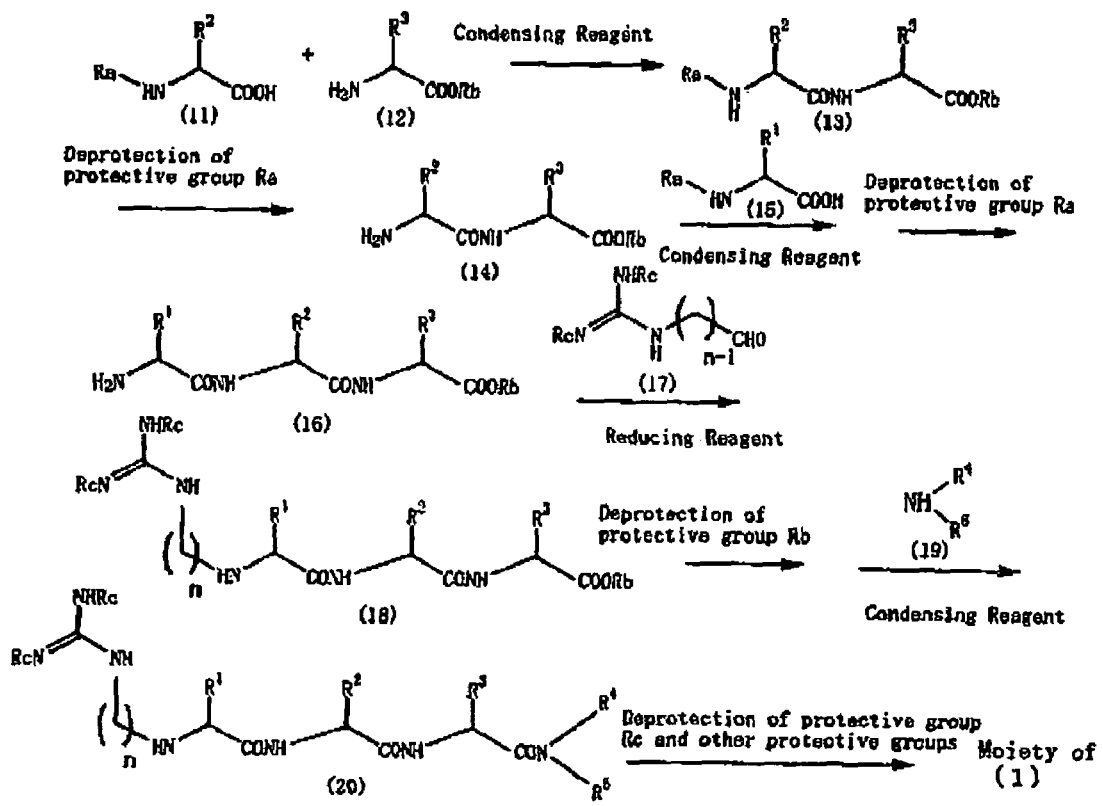
FIGS. 1 and 2 show reaction sequences for preparing compounds of this invention.

A compound (1) of the present invention can be produced by the following method [1] (see FIG. 1 or [2] (see FIG. 2):

cleaving the protective group Rb for a carboxyl group followed by a reaction with an amino compound (19) in the present of a suitable condensing agent, a compound (20) is obtained. By cleaving all of the protective groups for amino groups and the like, a moiety of a compound (1) of the present invention wherein A is alkylene, and X and Y are —CONH— can be obtained.

Examples of the condensing agent employed in each of the above described production method or the condensation method may include a method employing N,N'-dicyclohexylcarbodiimide (hereinafter abbreviated as "DCC"), a method employing DCC and 1-hydroxybenzotriazole, a method employing 1-ethyl-3-(3-dimethylaminopropyl)carbodiimide and 1-hydroxybenzotriazole, a method employing 1,1'-carbonyldiimidazole or a method employing isobu-

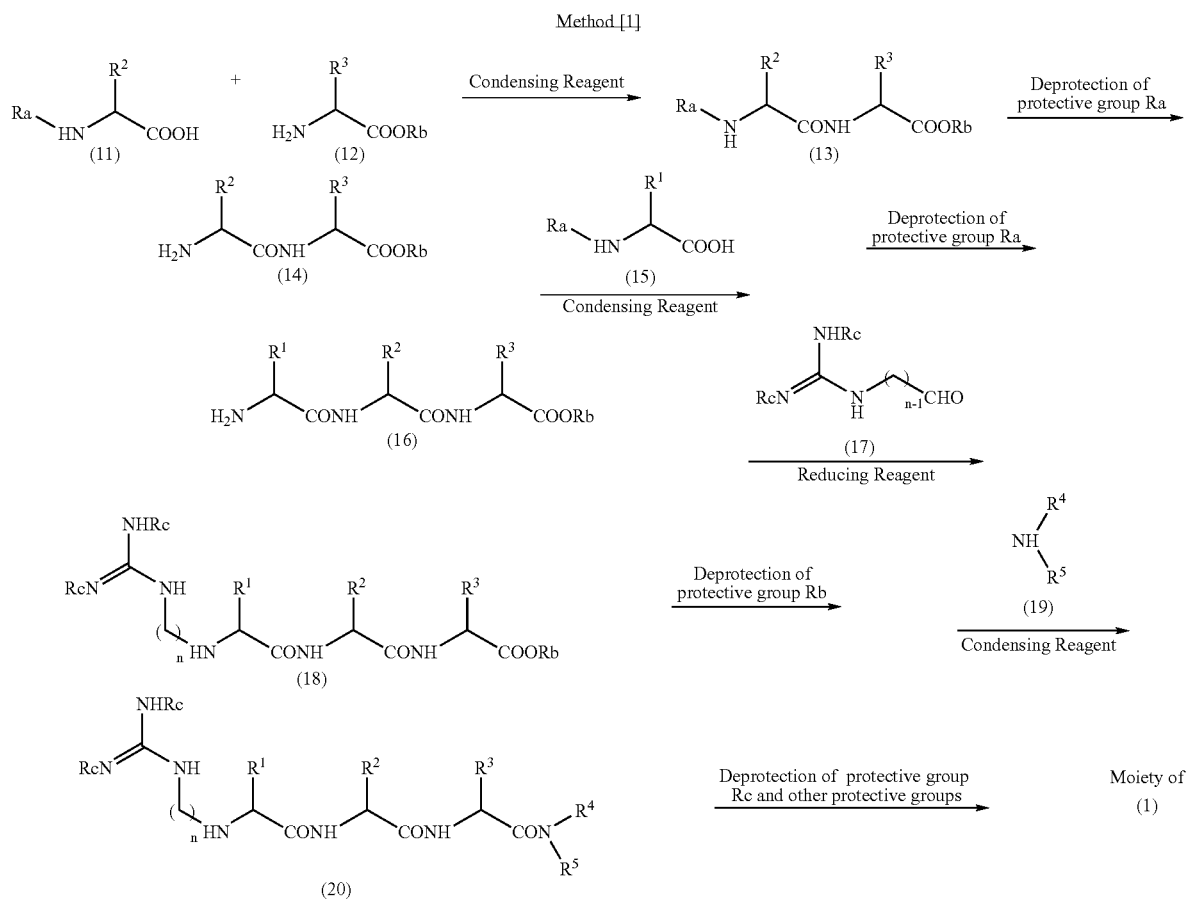

Wherein, in FIG. 1, $R^1$ to $R^5$ and n are defined as described above; Ra and Rc represents protective groups for amino groups and Rb represents a protective group.

As shown in FIG. 1, amino acid derivates (11) and (12) are reacted in the presence of a suitable condensing agent to obtain a compound (13), which is then subjected to the deprotection of the protective group for an amino group and fused with an amino derivative (15), and thereafter subjected again to the deprotection of the protective group for an amino group, thereby obtaining an amino compound (16). This is then reacted with an aldehyde (17), and then treated with a reducing agent to obtain a compound (18). After tyl chloroformate or diphenylphosphoryl azide in the presence of triethylamine and the like.

Examples of the reducing agent employed in each of the above described production methods may include a metal hydride compound such as sodium cyanoborohydride, sodium borohydride and lithium aluminum hydride or a dimethylamine-borane complex.

Examples of the protective group for the amino group employed in each of the above described production methods may include benzyloxycarbonyl, tert-butoxycarbonyl, formyl, trityl, chloroacetyl, trialkylsilyl, benzyl and 9-fluorenylmethoxycarbonyl. Examples of the protective group for the carboxyl group may include methyl, ethyl, benzyl and phenacyl.

Examples of the protective group for the amino acid side chain of the amino acid derivative employed in each of the above described production method, for example in the case of arginine, may include a 4-methoxy-2,3,6-trimethlbenzenesulfonyl group (Mtr), a 2,2,4,6,7-pentamethyldihydrobenzofuran-5-sulfonyl group (Pmc) and tert-butoxycarbonyl, while that in the case of tyrosine may include tert-butyl and benzyl.

The above described protective groups can be introduced and cleaved by a standard method, for example, by a method described in a reference (T. W. Greene, et al., "Protective Groups in Organic Synthesis", John Wiley & Sons, Inc., New York, 1999, p. 17–292, p. 369–653, p701–747).

There are used, as a solvent for a condensation reaction or for the introduction or cleavage of a protective group in the above described production method, absolute or hydrated alcohols, organic acids, esters, halogenated hydrocarbons, ketones and aprotic polar solvents or a mixture solvent thereof.

Examples of the absolute or hydrated alcohols may include absolute or hydrated methanol, absolute or hydrated ethanol and the like, examples of the organic acids may include acetic acid, trifluoroacetic acid and the like, examples of the esters may include ethyl acetate, methyl acetate and the like, examples of the ethers may include diisopropyl ether, diethyl ether, tetrahydrofuran and the like, examples of the halogenated hydrocarbons may include dichloromethane, dichloroethane, chloroform and the like, examples of the ketones may include acetone, ethyl methyl ketone and the like, and examples of the aprotic polar solvents may include dimethyl sulfoxide, N,N'-dimethyl formamide and the like.

The reaction temperature in each production method is −20 to 100° C., preferably 0 to 50° C., more preferably 10 to 30° C. The reaction temperature in deprotecting a protective group is −10 to 80° C., preferably 0 to 50° C., more preferably 5 to 20° C.

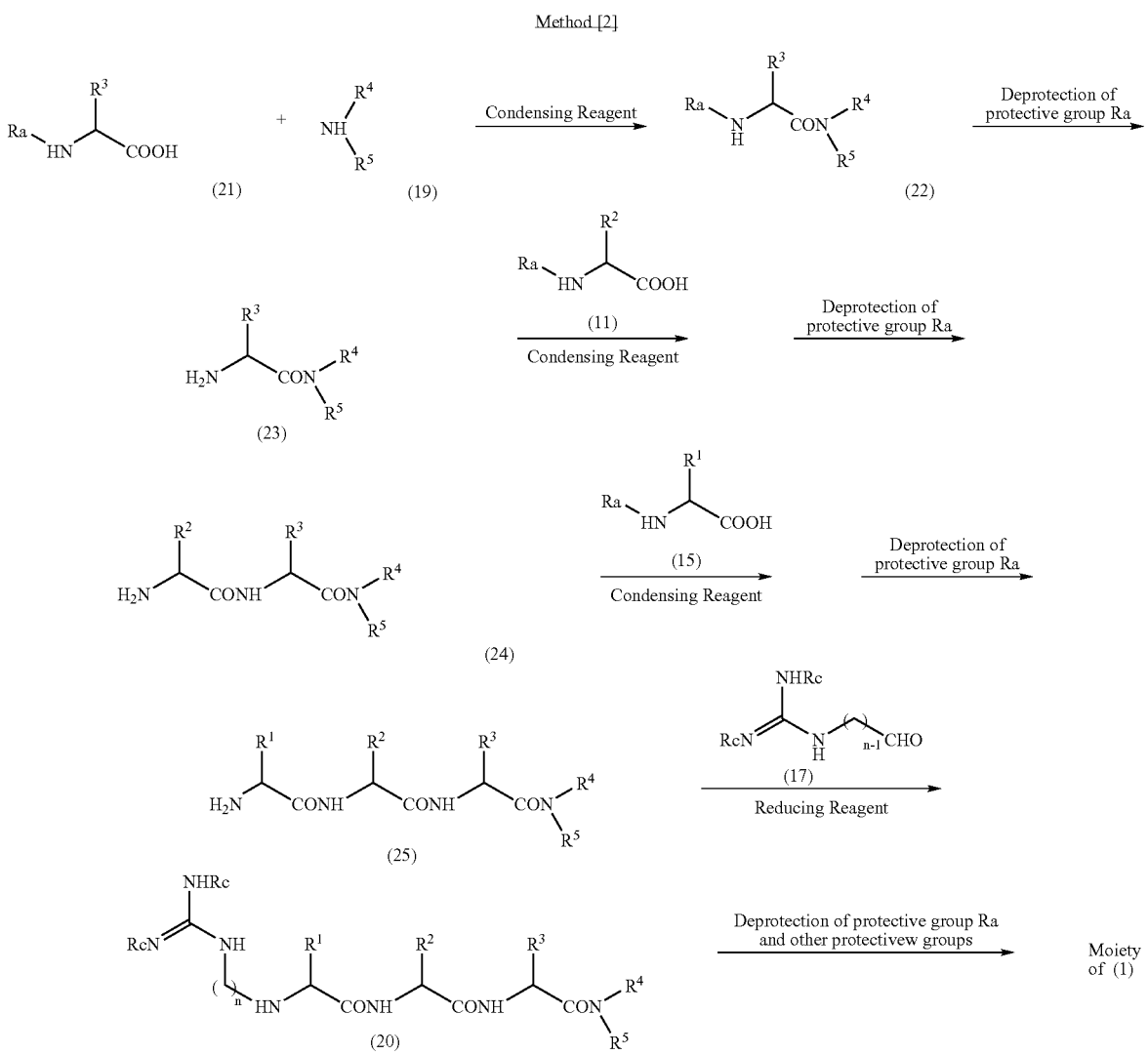

Figure 2:
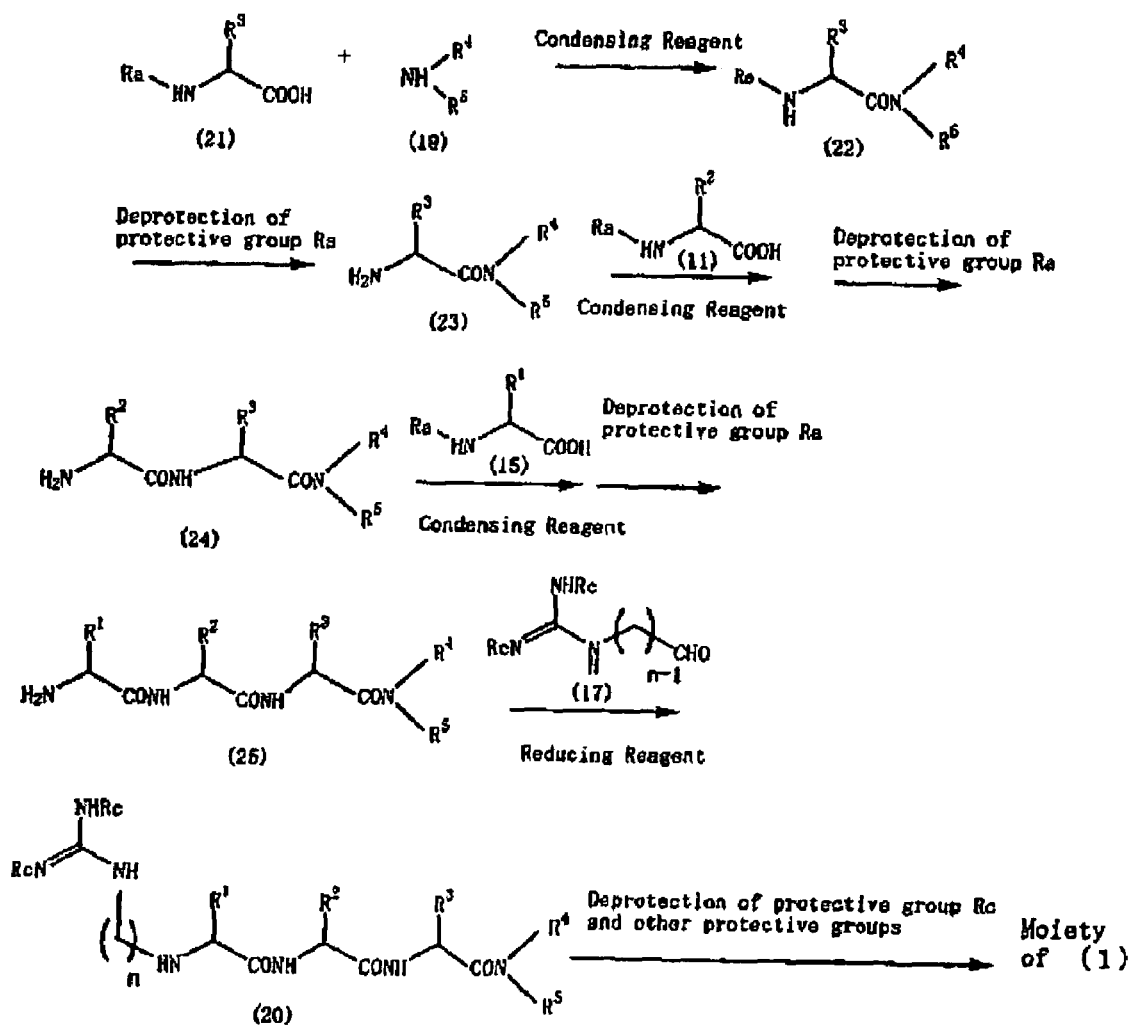

In FIG. 2, $R^1$ to $R^5$ are defined as described above; and Ra and Rc represents protective groups for amino groups.

As shown in FIG. 2, an amino acid derivative (21) and an amino compound (19) are reacted in the presence of a suitable condensing agent to obtain a compound (22), which is then subjected to the deprotection of the protective group for an amino group and fused with an amino acid derivative (11), and thereafter subjected again to the deprotection of the protective group for an amino group, followed by the condensation with an amino acid derivative (15) followed again by the deprotection of the protective group for an amino group, thereby obtaining an amino compound (25). This is then reacted with an aldehyde (17), and then treated with a reducing agent to obtain a compound (20). Then, by cleaving all of the protective groups for amino groups and the like, a moiety of a compound (1) of the present invention wherein A is alkylene, and X and Y are —CONH— can be obtained.

The reaction in each step can be performed as described above.

The compound of the present invention or its salt thus produced may be purified into a free base form, free acid form, acid addition salt form, metal salt form, d form, l form or dl mixture form by a method known per se such as condensation, liquid phase conversion, partition, solvent extraction, crystallization, fractionation, chromatography and the like.

When the compound according to the present invention is administered as a pharmaceutical, the compound of general formula (1) or its salt may be given as it is or in a pharmaceutical composition containing it at a concentration of 0.1 to 99.5%, preferably 0.5 to 90% in a pharmaceutically acceptable non-toxic inert carrier.

As the carrier, there is used at least one of solid, semi-solid or liquid diluent, filler and other auxiliary agents in the formulation. The compound expressed by general formula (1) or its salt is given preferably as a unit dosage form. While the compound expressed by general formula (1) or its salt can exert its effect when given orally, it can exert its effect also when given by an intra-tissue administration (such as intravenous injection), topical administration (percutaneous administration, instillation, nasal administration) or rectal administration.

While the dosage of the compound according to the present invention as a pharmaceutical may be adjusted preferably with taking the age, body weight condition of the patient, administration route, nature and degree of the disease into consideration, it is usually 0.1 to 1000 mg daily as the compound according to the present invention in adult, preferably 1 to 500 mg. A more or less dosage may sometimes be required. The number of dosage may be divided into 2 to 3 times in a day.

The oral administration can be accomplished in the form of powder, tablet, capsule, sugar-coated tablet, granule, dust, suspension, liquid, syrup, drop, buccal formulation or other formulations.

The powder formulation can be produced by pulverizing the compound expressed by general formula (1) or the salt thereof into particles having suitable sizes.

The dust formulation can be produced by pulverizing the compound expressed by general formula (1) or the salt thereof into particles having suitable sizes followed by mixing with a similarly pulverized pharmaceutical carrier, for example an edible carbohydrate such as starch, mannitol and the like. If necessary, other additives such as seasonings, preservatives, dispersing agents, colorants and flavors may also be added.

The tablet formulation can be produced by preparing a powder mixture containing an excipient, granulating or slugging, adding a disintegrant or lubricant and then compacting into tablets.

The powder mixture is prepared by mixing a suitably pulverized compound with the above described diluent or base if necessary together with binders (for example, sodium carboxymethyl cellulose, methyl cellulose, hydroxypropyl-methyl cellulose, gelatin, polyvinyl pyrrolidone, polyvinyl alcohol and the like), dissolution retardants (for example, paraffin and the like), adsorbents (for example, bentonite, kaolin, dicalcium phosphate and the like).

A powder mixture is first made wet using a binder such as a syrup, starch, gum arabic, cellulose solution or a polymer solution, and then agitated and mixed, dried and pulverized to obtain a granule.

Instead of granulating a powder, a compacting machine is used first to obtain an incompletely shaped slug, which is then pulverized to obtain a granule. The granule thus obtained can be made free of adhesion to each other by adding stearic acid, stearates, talc, mineral oil and the like as a lubricant. The plane tablet thus obtained may be film-coated or sugar-coated.

The compound expressed by general formula (1) or its salt can also be compacted directly after mixing with a flowable inert carrier. A transparent or opaque protective film formed as a closely covering shellac coating, a sugar or polymeric film and a glossy film of a wax may also be employed.

A capsule formulation can be produced by filling a powder, dust or granule formulation for example in an encapsulating shell such as a gelatin capsule. The compaction may be accomplished also after mixing the powdery material with a lubricant or fluidizing agent such as colloidal silica, talc, magnesium stearate, calcium stearate, solid polyethylene glycol and the like. The efficacy of a pharmaceutical after the ingestion of a capsule formulation can be enhanced by adding a disintegrant or solubilizing agent such as carboxymethyl cellulose, calcium carboxymethyl cellulose, low-substituted hydroxypropyl cellulose, calcium croscarmellose, sodium carboxymethyl starch, calcium carbonate, sodium carbonate and the like. A compound expressed by general formula (1) or its salt may be suspended and dispersed in a vegetable oil, polyethylene glycol, glycerin or surfactant and then encapsulated in a gelatin sheet to obtain a soft capsule formulation.

Other oral formulations such as solutions, syrups, troches, elixirs and nasal formulations may be presented as a unit dosage form containing a certain amount of a compound expressed by general formula (1) or a salt thereof. For producing an ointment, fats, oils, lanolin, petrolatum, paraffin, wax, resins, plastics, glycols, higher alcohols, glycerin, water, emulsifier, suspending agent or other suitable additives are employed as starting material or bases, to which a compound expressed by general formula (1) or its salt is added and mixed. A poultice formulation can be produced by mixing a powder of a compound expressed by general formula (1) or a salt thereof with a suitable liquid material such as glycerin, water and the like followed by adding an essential oil component. For producing a plaster formulation, fats, oils, fatty acid salts, wax, resins, plastics, purified lanolin, rubber or a mixture thereof are employed as starting material or bases, to which a compound expressed by general formula (1) or its salt is admixed uniformly. An eye drop formulation can be produced by dissolving or suspending a certain amount of a compound expressed by general

EXAMPLE 1

N-α-6-Guanidinohexyl-L-tyrosyl-L-tyrosyl-L-arginyl-L-tryptophanamide (SEQ. ID. NO 2)

Step 1

N-ω-(2,2,5,7,8-Pentamethylchroman-6-sulfonyl)-L-arginyl-L-tryptophanamide

N-α-9-fluorenylmethoxycarbonyl-N-ω-(2,2,5,7,8-pentamethylchroman-6-sulfonyl)-L-arginine (2.0 g, 3.0 mmol) was dissolved in DMF (15 mL), combined with 1-hydroxybenzotriazole (449 mg, 3.3 mmol) and 1-ethyl-3-(3-dimethylaminopropyl)carbodiimide hydrochloride (WSC; 636 mg, 3.3 mmol) and stirred at room temperature for 10 minutes. This was cooled to 0° C., L-tryptophanamide hydrochloride (723 mg, 3.0 mmol) and N,N-diisopropylethylamine (0.53 mL) were added, and the mixture was stirred further at room temperature overnight. The reaction solution was extracted with ethyl acetate, washed with a saturated aqueous solution of sodium hydrogen carbonate, saturated brine and water. The organic layer was dried over sodium sulfate, filtered through a cotton plug to remove solids, and washed with ethyl acetate. The filtrate and the wash were combined and concentrated under reduced pressure. The resultant syrup was combined with a 10% piperidine/DMF solution (30 mL) to dissolve, and stirred at room temperature for 20 minutes. The reaction solution was concentrated under reduced pressure, and the resultant residue was subjected to column chromatography to obtain N-ω-(2,2,5,7,8-pentamethylchroman-6-sulfonyl)-L-arginyl-L-tryptophanamide (compound 1; yield: 1.8 g).

Step 2

O-tert-Butyl-L-tyrosyl-N-ω-(2,2,5,7,8-pentamethylchroman-6-sulfonyl)-L-arginyl-L-tryptophanamide N-α-9-fluorenylmethoxycarbonyl-O-tert-butyl-L-tyrosine (1.4 g, 3.0 mmol) and the compound 1 (1.8 g, 2.9 mmol) were reacted in accordance with the method for synthesizing the compound 1 to obtain O-tert-butyl-L-tyrosyl-N-ω-(2,2,5,7,8-pentamethylchroman-6-sulfonyl)-L-arginyl-L-tryptophanamide (compound 2; yield: 2.4 g).

Step 3

O-tert-Butyl-L-tyrosyl-O-tert-butyl-L-tyrosyl-N-ω-(2,2,5,7,8-pentamethylchroman-6-sulfonyl)-L-arginyl-L-tryptophanamide N-α-9-fluorenylmethoxycarbonyl-O-tert-butyl-L-tyrosine (674 mg, 1.5 mmol) and the compound 2 (1.2 g, 1.4 mmol) were reacted in accordance with the method for synthesizing the compound 1 to obtain O-tert-butyl-L-tyrosyl-O-tert-butyl-L-tyrosyl-N-ω-(2,2,5,7,8-pentamethylchroman-6-sulfonyl)-L-arginyl-L-tryptophanamide (compound 3; yield: 1.3 g).

Step 4

6-(2,3-di-tert-Butoxycarbonyl)guanidino-1-hexanol

6-Amino-1-hexanol (1.2 g, 10.2 mmol) was dissolved in methylene chloride (10 mL), combined with 1,3-bis(tert-butoxycarbonyl)-2-methyl-2-thiopseudourea (3.97 g, 13.7 mmol) and stirred overnight. The reaction solution was concentrated under reduced pressure, and the residue was subjected to a column chromatography to obtain 6-(2,3-di-tert-butoxycarbonyl)guanidino-1-hexanol (compound 4; yield: 3.5 g)

Step 5

6-(2,3-di-tert-Butoxycarbonyl)guanidino-1-hexanal

The compound 4 (169 mg, 0.47 mmol) was dissolved in methylene chloride (5 mL), combined with Dess-Martin reagent (700 mg, 1.7 mmol) and stirred for 15 minutes. After completion of the reaction, the reaction solution was combined with a saturated aqueous solution of sodium hydrogen carbonate and an aqueous solution of sodium thiosulfate, stirred for 15 minutes, and extracted with ether. The organic layer was dried over sodium sulfate, made free of solids by filtration through a cotton plug, and then washed with ether. The filtrate and the wash were combined and concentrated under reduced pressure to obtain a crude 6-(2,3-di-tert-butoxycarbonyl)guanidino-1-hexanal (compound 5)(166 mg).

Step 6

N-α-6-(2,3-di-tert-butoxycarbonyl)guanidinohexyl-(O-tert-butyl)-L-tyrosyl-(O-tert-butyl)-L-tyrosyl-N-ω-(2,2,5,7,8-pentamethylchroman-6-sulfonyl)-L-arginyl-L-tryptophanamide (SEQ. ID. NO. 1)

The compound 3 (250 mg, 0.23 mmol) and a crude product of the compound 5 (166 mg) were dissolved in methanol (3.5 mL), adjusted at pH4 with acetic acid, and stirred at room temperature for 15 minutes. The reaction solution was cooled to 0° C., combined with sodium cyanoborohydride (59.2 mg, 0.94 mmol), and stirred at room temperature further for 30 minutes. After completion of the reaction, the reaction solution was concentrated under reduced pressure, and the resultant residue was extracted with ethyl acetate, and the organic layer washed with a saturated aqueous solution of sodium hydrogen carbonate, a saturated brine and water. The organic layer was dried over sodium sulfate, made free of solids by filtration through a cotton plug, and washed with ethyl acetate. The filtrate and the wash were combined and concentrated under reduced pressure, and the resultant residue was subjected to a column chromatography to obtain N-α-6-(2,3-di-tert-butoxycarbonyl)guanidinohexyl-(O-tert-butyl)-L-tyrosyl-(O-tert-butyl)-L-tyrosyl-N-ω-(2,2,5,7,8-pentamethylchroman-6-sulfonyl)-L-arginyl-L-tryptophanamide (compound 6; yield: 174 mg).

Step 7

N-α-6-Guanidinohexyl-L-tyrosyl-L-tyrosyl-L-arginyl-L-tryptophanamide (SEQ. ID. NO 2)

The compound 6 (350 mg, 0.25 mmol) was dissolved in a mixture of trifluoroacetic acid (12 mL), phenol (900 mg), ethanedithiol (0.3 mL), thioanisole (0.6 mL) and water (0.6 mL), and stirred at room temperature for 2 hours. After completion of the reaction, the reaction solution was poured into ether, and subjected to a centrifuge to obtain a pellet.

This was subjected to a high pressure liquid column chromatography to obtain N-α-6-guanidinohexyl-L-tyrosyl-L-tyrosyl-L-arginyl-L-tryptophanamide (compound 7; 160 mg, 78%).

FAB MS [M+H]⁺=827

EXAMPLE 2

N-α-4-Guanidinobutyryl-L-tyrosyl-L-tyrosyl-L-arginyl-L-tryptophanamide (SEQ. ID. NO 2)

Step 1

4-(2,3-di-tert-Butoxycarbonylguanidino)butyric acid

4-Aminobutyric acid (100 mg, 0.97 mmol) was dissolved in tetrahydrofuran (0.3 mL) and water (0.03 mL), combined with 1,3-bis(tert-butoxycarbonyl)-2-methyl-2-thiopseudourea (340 mg, 1.2 mmol) and stirred at 60° C. overnight. The reaction solution was concentrated under reduced pressure, and the residue was subjected to a column chromatography to obtain 4-(2,3-di-tert-butoxycarbonylguanidino)butyric acid (compound 8; yield: 181 mg).

Step 2

N-α-[4-(2,3-di-tert-Butoxycarbonyl)guanidinobutyryl]-(O-tert-butyl)-L-tyrosyl-(O-tert-butyl)-L-tyrosyl-N-ω-(2,2,5,7,8-pentamethylchroman-6-sulfonyl)-L-arginyl-L-tryptophanamide (SEQ. ID. NO. 1)

The compound 3 (200 mg, 0.19 mmol) and the compound 8 (84.4 mg, 0.24 mmol) were reacted in accordance with the method for synthesizing the compound 1 to obtain N-α-[4-(2,3-di-tert-butoxycarbonyl)guanidinobutyryl]-(O-tert-butyl)-L-tyrosyl-(O-tert-butyl)-L-tyrosyl-[N-ω-(2,2,5,7,8-pentamethylchroman-6-sulfonyl)]-L-arginyl-L-tryptophanamide (compound 9; yield: 212 mg).

Step 3

N-α-4-Guanidinobutyryl-L-tyrosyl-L-tyrosyl-L-arginyl-L-tryptophanamide (SEQ. ID. NO 2)

The compound 9 (100 mg, 0.07 mmol) was reacted in accordance with the method for synthesizing the compound 7 to obtain N-α-4-guanidinobutyryl-L-tyrosyl-L-tyrosyl-L-arginyl-L-tryptophanamide (compound 10; yield: 42 mg).

FAB MS [M+H]⁺=813

EXAMPLE 3

N-α-6-Guanidinohexyl-L-tyrosyl]-N-[5-amino-(S)-1-[[N-2-(3-indolyl)ethyl]aminomethyl]pentyl]-L-tyrosinamide (SEQ. ID. NO 2)

Step 1

N-9-Fluorenylmethoxycarbonyl-N-ε-tert-butoxycarbonyl-lysinal

N-9-fluorenylmethoxycarbonyl-N-ε-tert-butoxycarbonyl-lysinol (200 mg, 0.44 mmol) was dissolved in methylene chloride (5 mL), combined with Dess-Martin reagent (746 mg, 1.8 mmol) and stirred at room temperature for 15 minutes. After completion of the reaction, the reaction solution was combined with a saturated aqueous solution of sodium hydrogen carbonate and a saturated aqueous solution of sodium thiosulfate, stirred for 15 minutes, and then extracted with ether. The organic layer was dried over sodium sulfate, made free of solids by filtration through a cotton plug, and then washed with ether. The filtrate and the wash were combined and concentrated under reduced pressure to obtain a crude product of N-9-fluorenylmethoxycarbonyl-N-ε-tert-butoxycarbonyl-lysinal (compound 11) (199 mg).

Step 2

6-(N-tert-Butoxycarbonyl)amino-(S)-2-(N-9-fluorenylmethoxycarbonyl)amino-N-[2-(3-indolyl)ethyl]hexylamine Tryptamine (198 mg, 1.2 mmol) and a crude product of the compound 11 (279 mg, 0.62 mmol) were dissolved in methanol (12 mL), adjusted at pH4 with acetic acid, and then stirred at room temperature for 15 minutes. The reaction solution was cooled to 0° C., combined with sodium cyanoborohydride (200 mg, 3.2 mmol) and stirred further at room temperature overnight. After completion of the reaction, the reaction solution was concentrated under reduced pressure, the resultant residue was extracted with ethyl acetate, and the organic layer washed with a saturated aqueous solution of sodium hydrogen carbonate, saturated brine and water. The organic layer was dried over sodium sulfate, made free of solids by filtration through a cotton plug, and washed with ethyl acetate. The filtrate and the wash were combined and concentrated under reduced pressure, and the resultant residue was subjected to a column chromatography to obtain 6-(N-tert-butoxycarbonyl)amino-(S)-2-(N-9-fluorenylmethoxycarbonyl)amino-N-[2-(3-indolyl)ethyl]hexylamine (compound 12; yield: 250 mg).

Step 3

6-(N-tert-Butoxycarbonyl)amino-(S)-2-(N-9-fluorenylmethoxycarbonyl)amino-N-butoxycarbonyl-N-[2-(3-indolyl)ethyl]hexylamine The compound 12 (250 mg, 0.42 mmol) was dissolved in methylene chloride (6 mL), cooled to 0° C., combined with di-tert-butyl dicarbonate (110 mg, 0.50 mmol) and triethylamine (0.1 mL), and then stirred further at room temperature for 30 minutes. After completion of the reaction, the reaction solution was concentrated under reduced pressure, the resultant residue was subjected to a column chromatography to obtain 6-(N-tert-butoxycarbonyl)amino-(S)-2-(N-

9-fluorenylmethoxycarbonyl)amino-N-butoxycarbonyl-N-[2-(3-indolyl)ethyl]hexylamine (compound 13; yield: 204 mg).

Step 4

6-(N-tert-Butoxycarbonyl)amino-(S)-2-amino-N-butoxycarbonyl-N-[2-(3-indolyl)ethyl]hexylamine The compound 13 (195 mg, 0.78 mmol) was dissolved in a 10% piperidine/DMF solution, and stirred at room temperature for 20 minutes. This reaction solution was concentrated under reduced pressure, and the resultant residue was subjected to a column chromatography to obtain 6-(N-tert-butoxycarbonyl)amino-(S)-2-amino-N-butoxycarbonyl-N-[2-(3-indolyl)ethyl]hexylamine (compound 14; yield: 129 mg).

Step 5

N'-α-9-Fluorenylmethoxycarbonyl-N-[5-(N'-tert-butoxycarbonyl)amino-(S)-1-[[N'-tert-butoxycarbonyl-N-[2-(3-indolyl)ethyl]aminomethyl]pentyl]-L-tyrosinamide N-α-9-fluorenylmethoxycarbonyl-O-tert-butyl-L-tyrosine (133 mg, 0.29 mmol) was dissolved in DMF (1 mL), combined with 1-hydroxybenzotriazole (43 mg, 0.32 mmol) and 1-ethyl-3-(3-dimethylaminopropyl)carbodiimide hydrochloride (WSC; 61 mg, 0.32 mmol) and stirred at room temperature for 10 minutes. This was cooled to 0° C., combined with the compound 14 (125 mg, 0.26 mmol) dissolved in DMF (2 mL), and stirred further at room temperature overnight. The reaction solution was extracted with ethyl acetate, washed with a saturated aqueous solution of sodium hydrogen carbonate, saturated brine and water. The organic layer was dried over sodium sulfate, made free of solids by filtration through a cotton plug, and washed with ethyl acetate. The filtrate and the wash were combined and concentrated under reduced pressure, and the resultant residue was subjected to a column chromatography to obtain N'-α-9-fluorenylmethoxycarbonyl-N-[5-(N-tert-butoxycarbonyl)amino-(S)-1-[N-tert-butoxycarbonyl-N-[2-(3-indolyl)ethyl]aminomethyl]pentyl]-L-tyrosinamide (compound 1; yield: 221 mg).

Step 6

N-[5-(N-tert-Butoxycarbonyl)amino-(S)-1-[N-tert-butoxycarbonyl-N-[2-(3-indolyl)ethyl]aminomethyl]pentyl]-(O-tert-butyl)-L-tyrosinamide The compound 15 (210 mg, 0.23 mmol) was synthesized by the method similar to that for the compound 14 to obtain N-[5-(N'-tert-butoxycarbonyl)amino-(S)-1-[N-tert-butoxycarbonyl-N-[2-(3-indolyl)ethyl]aminomethyl]pentyl]-(O-tert-butyl)-L-tyrosinamide (compound 16; yield: 80 mg).

Step 7

N-α-[6-(2,3-di-tert-Butoxycarbonyl)guanidino-hexyl]-(O-tert-butyl)-L-tyrosine methyl ester O-tert-butyl-L-tyrosine methyl ester (200 mg, 0.69 mmol) and a crude product of the compound 5 (320 mg, 0.89 mmol) were dissolved in methanol (3 mL), adjusted at pH4 with acetic acid, and then stirred at room temperature for 15 minutes. The reaction solution was cooled to 0° C., combined with sodium cyanoborohydride (285 mg, 4.5 mmol), and then stirred further at room temperature for 90 minutes. After completion of the reaction, the reaction solution was concentrated under reduced pressure, and the resultant residue was extracted with ethyl acetate, and the organic layer was washed with a saturated aqueous solution of sodium hydrogen carbonate, saturated brine and water. The organic layer was dried over sodium sulfate, made free of solids by filtration through a cotton plug, and washed with ethyl acetate. The filtrate and the wash were combined and concentrated under reduced pressure, and the resultant residue was subjected to a column chromatography to obtain N-α-[6-(2,3-di-tert-butoxycarbonyl)guanidinohexyl]-(O-tert-butyl)-L-tyrosine methyl ester (compound 17; yield: 299 mg).

Step 8

N-α-[6-(2,3-di-tert-Butoxycarbonylguanidino)hexyl]-(O-tert-butyl)-L-tyrosine methyl ester The compound 17 (289 mg, 0.49 mmol) was dissolved in methylene chloride (5 mL), cooled to 0° C., combined with di-tert-butyl dicarbonate (426 mg, 2.0 mmol) and triethylamine (0.4 mL), and stirred further at 40° C. overnight. After completion of the reaction, the reaction solution was combined with ethyl acetate, and the organic layer was washed with a 6% aqueous solution of potassium hydrogen sulfate and a saturated aqueous solution of sodium hydrogen carbonate. The organic layer was dried over sodium sulfate, made free of solids by filtration through a cotton plug, and washed with ethyl acetate. The filtrate and the wash were combined and concentrated under reduced pressure, and the resultant residue was subjected to a column chromatography to obtain N-α-[6-(2,3-di-tert-butoxycarbonylguanidino)hexyl]-(O-tert-butyl)-L-tyrosine methyl ester (compound 18; yield: 241 mg).

Step 9

N-α-6-(2,3-di-tert-Butoxycarbonyl) guanidinohexyl-N-α-tert-butoxycarbonyl-(O-tert-butyl)-L-tyrosyl-N-[5-(N-tert-butoxycarbonyl)amino-(S)-1-[N-tert-butoxycarbonyl-N-[2-(3-indolyl)ethyl]aminomethyl]pentyl]-(O-tert-butyl)-L-tyrosinamide The compound 18 (113 mg, 0.16 mmol) was dissolved in tetrahydrofuran (3 mL), methanol (0.5 mL) and water (0.3 mL), combined with lithium hydroxide monohydrate (22 mg, 0.52 mmol) and stirred at room temperature for 2 hours. After completion of the reaction, the reaction solution was combined with ethyl acetate, and the organic layer was washed with a 6% aqueous solution of potassium hydrogen sulfate. The organic layer was dried over sodium sulfate, made free of solids by filtration through a cotton plug, washed with ethyl acetate, and the filtrate and the wash were combined and concentrated under reduced pressure. The resultant syrup was dissolved in a 5% 1-hydroxybenzotriazole/DMF solution (3 mL), combined with the compound 16 (75 mg, 0.11 mmol), benzotriazol-1-yl-oxy-tris-pyrrolidino-phosphonium hexafluorophosphate (PyBOP; 95 mg, 0.18 mmol) and N,N-diisopropylethylamine (0.06 mL, 0.36 mmol) and stirred at room temperature overnight. The reaction solution was extracted with ethyl acetate, washed with a saturated aqueous solution of sodium hydrogen carbonate, saturated brine and water. The organic layer was dried over sodium sulfate, made free of solids by filtration through a cotton plug, and washed with ethyl acetate. The filtrate and the wash were combined and concentrated under reduced pressure, and the resultant residue was subjected to a column chromatography to obtain N-α-6-(2,3-di-tert-butoxycarbonyl)guanidinohexyl-N-α-tert-butoxycarbonyl-(O-tert-butyl)-L-tyrosyl-N-[5-(N-tert-butoxycarbonyl)amino-(S)-1-[N-tert-butoxycarbonyl-N-[2-(3-indolyl)ethyl] aminomethyl]pentyl]-(O-tert-butyl)-L-tyrosinamide (compound 19; yield: 80 mg).

Step 10

N-α-6-Guanidinohexyl-L-tyrosyl-N-[5-amino-(S)-1-[[N-2-(3-indolyl)ethyl]aminomethyl]pentyl]-L-tyrosinamide The compound 19 (80 mg, 0.06 mmol) was dissolved in a mixture of trifluoroacetic acid (2.7 mL), ethanedithiol (0.15 mL) and water (0.15 mL), and stirred at room temperature for 2 hours. After completion of the reaction, the reaction solution was poured into ether, and subjected to a centrifuge to obtain a pellet. This was subjected to a high pressure column chromatography to obtain N-α-6-guanidinohexyl-L-tyrosyl-N-[5-amino-(S)-1-[[N-2-(3-indolyl) ethyl]aminomethyl]pentyl]-L-tyrosinamide (compound 20; yield: 33 mg).

FAB MS [M+H]$^+$=742

EXAMPLE 4

N-α-6-Guanidinohexyl-L-3-(2-naphthyl)-alanyl-N-[5-amino-(S)-1-[[N-[(S)-1-hydroxymethyl-2-(3-indolyl)]ethyl]aminomethyl]pentyl]-L-3-(2-naphthyl)-alaninamide Step 1

6-(N-tert-Butoxycarbonyl)amino-(S)-2-(N-9-fluorenylmethoxycarbonyl)amino-N-[(S)-1-hydroxymethyl-2-(3-indolyl)ethyl]hexylamine L-Tryptophanol (410 mg, 2.2 mmol) and a crude product of the compound 11 (500 mg, 1.1 mmol) were dissolved in methanol (15 mL), adjusted at pH4 with acetic acid, and then stirred at room temperature for 15 minutes. The reaction solution was cooled to 0° C., combined with sodium cyanoborohydride (346 mg, 5.5 mmol) and stirred further at room temperature overnight. After completion of the reaction, the reaction solution was concentrated under reduced pressure, and the resultant residue was extracted with ethyl acetate, and the organic layer was washed with a saturated aqueous solution of sodium hydrogen carbonate, saturated brine and water. The organic layer was dried over sodium sulfate, made free of solids by filtration through a cotton plug, and washed with ethyl acetate. The filtrate and the wash were combined and concentrated under reduced pressure, and the resultant residue was subjected to a column chromatography to obtain 6-(N-tert-butoxycarbonyl)amino-(S)-2-(N-9-fluorenylmethoxycarbonyl)amino-N-[(S)-1-hydroxymethyl-2-(3-indolyl)ethyl]hexylamine (compound 21; yield: 431 mg).

Step 2

N-α-9-Fluorenylmethoxycarbonyl-N-[5-(N-tert-butoxycarbonyl)amino-(S)-1-[[N-[(S)-1-hydroxymethyl-2-(3-indolyl)]ethyl]aminomethyl]pentyl]-L-3-(2-naphthyl)-alaninamide The compound 21 (350 mg, 0.56 mmol) was combined with a 10% piperidine/DMF solution (6 mL) and dissolved, stirred at room temperature for 20 minutes, and concentrated under reduced pressure. The resultant syrup was dissolved in a 5% 1-hydroxybenzotriazole/DMF solution (3 mL), combined with N-α-9-fluorenylmethoxycarbonyl-L-3-(2-naphthyl)-alanine (245 mg, 0.56 mmol), benzotriazole-1-yl-oxy-tris-pyrrolidino-phosphonium hexafluorophosphate (PyBOP; 320 mg, 0.62 mmol) and N,N-diisopropylethylamine (0.22 mL, 1.2 mmol) and stirred at room temperature overnight. The reaction solution was extracted with ethyl acetate, washed with a saturated aqueous solution of sodium hydrogen carbonate, a saturated brine and water. The organic layer was dried over sodium sulfate, made free of solids by filtration through a cotton plug, and washed with ethyl acetate. The filtrate and the wash were combined and concentrated under reduced pressure, and the resultant residue was subjected to a column chromatography to obtain N-α-9-fluorenylmethoxycarbonyl-N-[5-(N-tert-butoxycarbonyl)amino-(S)-1-[[N-[(S)-1-hydroxymethyl-2-(3-indolyl)]ethyl]aminomethyl]pentyl]-L-3-(2-naphthyl)-alaninamide (compound 22; yield: 405 mg).

Step 3

N-α-9-Fluorenylmethoxycarbonyl-L-3-(2-naphthyl)-alanyl-N-[5-(N-tert-butoxycarbonyl)amino-(S)-1-[[N-[(S)-1-hydroxymethyl-2-(3-indolyl)]ethyl]aminomethyl]pentyl]-L-3-(2-naphthyl)-alaninamide The compound 22 (350 mg, 0.42 mmol) was combined with a 10% piperidine/DMF solution (5 mL) and dissolved, stirred at room temperature for 20 minutes, and concentrated under reduced pressure. The resultant syrup was dissolved in a 5% 1-hydroxybenzotriazole/DMF solution (3 mL), combined with N-α-9-fluorenylmethoxycarbonyl-L-3-(2-naphthyl)-alanine (186 mg, 0.43 mmol), benzotriazole-1-yl-oxy-tris-pyrrolidino-phosphonium hexafluorophosphate (PyBOP; 243 mg, 0.47 mmol) and N,N-diisopropylethylamine (0.16 mL, 0.93 mmol) and stirred at room temperature for 2 hours. The reaction solution was extracted with ethyl acetate, washed with a saturated aqueous solution of sodium hydrogen carbonate, a saturated brine and water. The organic layer was dried over sodium sulfate, made free of solids by filtration through a cotton plug, and washed with ethyl acetate. The filtrate and the wash were combined and concentrated under reduced pressure, and the resultant residue was subjected to a column chromatography to obtain N-α-9-fluorenylmethoxycarbonyl-L-3-(2-naphthyl)-alanyl-N-[5-(N-tert-butoxycarbonyl)amino-(S)-1-[[N-[(S)-1-hydroxymethyl-2-(3-indolyl)]ethyl]aminomethyl]pentyl]-L-3-(2-naphthyl)-alaninamide (compound 23; yield: 337 mg).

Step 4

L-3-(2-naphthyl)-alanyl-N-[5-(N-tert-butoxycarbonyl)amino-(S)-1-[[N-[(S)-1-hydroxymethyl-2-(3-indolyl)]ethyl]aminomethyl]pentyl]-L-3-(2-naphthyl)-alaninamide The compound 23 (320 mg, 0.31 mmol) was reacted in accordance with the method for synthesizing the compound 7 to obtain L-3-(2-naphthyl)-alanyl-N-[5-(N-tert-butoxycarbonyl)amino-(S)-1-[[N-[(S)-1-hydroxymethyl-2-(3-indolyl)]ethyl]aminomethyl]pentyl]-L-3-(2-naphthyl)-alaninamide (compound 24; yield: 169 mg).

Step 5

N-α-6-(2,3-di-tert-Butoxycarbonyl)guanidinohexyl-L-3-(2-naphthyl)-alanyl-N-[5-(N'-tert-butoxycarbonyl)amino-(S)-1-[[N-[(S)-1-hydroxymethyl-2-(3-indolyl)]ethyl]aminomethyl]pentyl]-L-3-(2-naphthyl)-alaninamide The compound 24 (92 mg, 0.11 mmol) and a crude product of the compound 5 (68 mg, 0.19 mmol) were reacted in accordance with the method for synthesizing the compound 6 to obtain N-α-6-(2,3-di-tert-butoxycarbonyl)guanidinohexyl-L-3-(2-naphthyl)-alanyl-N-[5-(N'-tert-butoxycarbonyl)amino-(S)-1-[[N-[(S)-1-hydroxymethyl-2-(3-indolyl)]ethyl]aminomethyl]pentyl]-L-3-(2-naphthyl)-alaninamide (compound 25; yield: 64 mg).

Step 6

N-α-6-Guanidinohexyl-L-3-(2-naphthyl)-alanyl-N-[5-amino-(S)-1-[[N'-[(S)-1-hydroxymethyl-2-(3-indolyl)]ethyl]aminomethyl]pentyl]-L-3-(2-naphthyl)-alaninamide The compound 25 (64 mg, 0.06 mmol) was reacted in accordance with the method for synthesizing the compound 20 to obtain N-α-6-guanidinohexyl-L-3-(2-naphthyl)-alanyl-N-[5-amino-(S)-1-[[N'-[(S)-1-hydroxymethyl-2-(3-indolyl)]ethyl]aminomethyl]pentyl]-L-3-(2-naphthyl)-alaninamide (compound 26; yield: 14 mg).

FAB MS $[M+H]^+$=840

EXAMPLE 5

N-α-6-Guanidinohexyl-L-3-(1-naphthyl)-alanyl-L-tyrosyl-L-lysyl-L-tryptophanamide (SEQ. ID. NO 3)

Step 1

N-ε-tert-butoxycarbonyl-L-lysyl-L-tryptophanamide

N-α-9-fluorenylmethoxycarbonyl-N-ε-tert-butoxycarbonyl-lysine (5.9 g, 12.6 mmol) and L-tryptophanamide hydrochloride (3.0 g, 12.5 mmol) are reacted in accordance with the method for synthesizing the compound 1 to obtain N-ε-tert-butoxycarbonyl-L-lysyl-L-tryptophanamide (compound 27; yield: 5.3 g).

Step 2

O-tert-butyl-L-Tyrosyl-N-ε-tert-butoxycarbonyl-L-lysyl-L-tryptophanamide

N-α-9-fluorenylmethoxycarbonyl-O-tert-butyl-L-tyrosine (5.7 g, 12.3 mmol) and the compound 27 (5.3 g, 12.3 mmol) were reacted in accordance with the method for synthesizing the compound 1 to obtain O-tert-butyl-L-tyrosyl-N-ε-tert-butoxycarbonyl-L-lysyl-L-tryptophanamide (compound 28; yield: 7.7 g).

Step 3

N-α-9-Fluorenylmethoxycarbonyl-L-3-(1-naphthyl)-alanyl-(O-tert-butyl)-L-tyrosyl-N-ε-(tert-butoxycarbonyl)-L-lysyl-L-tryptophanamide N-α-9-fluorenylmethoxycarbonyl-L-3-(1-naphthyl)-alanine (168 mg, 0.38 mmol) was dissolved in DMF (2 mL), combined with 1-hydroxybenzotriazole (57 mg, 0.42 mmol) and 1-ethyl-3-(3-dimethylaminopropyl)carbodiimide hydrochloride (WSC; 81 mg, 0.42 mmol) and stirred at room temperature for 10 minutes. This was cooled to 0° C., combined with the compound 28 (250 mg, 0.38 mmol) and stirred further at room temperature overnight. The reaction solution was extracted with ethyl acetate, washed with a saturated aqueous solution of sodium hydrogen carbonate, a saturated brine and water. The organic layer was dried over sodium sulfate, made free of solids by filtration through a cotton plug, and washed with ethyl acetate. The filtrate and the wash were combined and concentrated under reduced pressure. The resultant residue was combined with petroleum ether to form a crystal, which was then recovered by filtration to obtain N-α-9-fluorenylmethoxycarbonyl-L-3-(1-naphthyl)-alanyl-(O-tert-butyl)-L-tyrosyl-N-ε-(tert-butoxycarbonyl)-L-lysyl-L-tryptophanamide (compound 29; yield: 359 mg).

Step 4

L-3-(1-Naphthyl)-alanyl-(O-tert-butyl)-L-tyrosyl-N-(tert-butoxycarbonyl)-L-lysyl-L-tryptophanamide The compound 29 (350 mg, 0.33 mmol) was reacted in accordance with the method for synthesizing the compound 14 to obtain L-3-(1-naphthyl)-alanyl-(O-tert-butyl)-L-tyrosyl-N-ε-(tert-butoxycarbonyl)-L-lysyl-L-tryptophanamide (compound 30; yield: 269 mg).

Step 5

N-α-[6-(2,3-di-tert-Butoxycarbonylguanidino)hexyl]-L-3-(1-naphthyl)-alanyl-(O-tert-butyl)-L-tyrosyl-N-ε-(tert-butoxycarbonyl)-L-lysyl-L-tryptophanamide (SEQ. ID. NO 4)

The compound 30 (100 mg, 0.12 mmol) and a crude product of the compound 5 (85 mg, 0.24 mmol) were reacted in accordance with the method for synthesizing the compound 6 to obtain N-α-[6-(2,3-di-tert-butoxycarbonylguanidino)hexyl]-L-3-(1-naphthyl)-alanyl-(O-tert-butyl)-L-tyrosyl-N-ε-(tert-butoxycarbonyl)-L-lysyl-L-tryptophanamide (compound 31; yield: 51 mg).

Step 6

N-α-6-Guanidinohexyl-L-3-(1-naphthyl)-alanyl-L-tyrosyl-L-lysyl-L-tryptophanamide (SEQ. ID. NO 3)

The compound 31 (51 mg, 0.04 mmol) was reacted in accordance with the method for synthesizing the compound 20 to obtain N-α-6-guanidinohexyl-L-3-(1-naphthyl)-alanyl-L-tyrosyl-L-lysyl-L-tryptophanamide (compound 32; yield: 27 mg).

FAB MS [M+H]$^+$=833

EXAMPLE 6

N-α-6-Guanidinohexyl-L-3-(2-naphthyl)-alanyl-L-tyrosyl-L-lysyl-L-tryptophanamide (SEQ. ID. NO 3)

Step 1

N-α-9-Fluorenylmethoxycarbonyl-L-3-(2-naphthyl)-alanyl-(O-tert-butyl)-L-tyrosyl-N-ε-(tert-butoxycarbonyl)-L-lysyl-L-tryptophanamide N-α-9-Fluorenylmethoxycarbonyl-L-3-(2-naphthyl)-alanine (168 mg, 0.38 mmol) was reacted in accordance with the method for synthesizing the compound 29 to obtain N-α-9-fluorenylmethoxycarbonyl-L-3-(2-naphthyl)-alanyl-(O-tert-butyl)-L-tyrosyl-N-ε-(tert-butoxycarbonyl)-L-lysyl-L-tryptophanamide (compound 33; yield: 355 mg).

Step 2

L-3-(2-Naphthyl)-alanyl-(O-tert-butyl)-L-tyrosyl-N-ε-(tert-butoxycarbonyl)-L-lysyl-L-tryptophanamide The compound 33 (350 mg, 0.33 mmol) was reacted in accordance with the method for synthesizing the compound 14 to obtain L-3-(2-naphthyl)-alanyl-(O-tert-butyl)-L-tyrosyl-N-ε-(tert-butoxycarbonyl)-L-lysyl-L-tryptophanamide (compound 34; yield: 276 mg).

Step 3

N-α-[6-(2,3-di-tert-butoxycarbonylguanidino)hexyl]-L-3-(2-naphthyl)-alanyl-(O-tert-butyl)-L-tyrosyl-N-ε-(tert-butoxycarbonyl)-L-lysyl-L-tryptophanamide The compound 34 (100 mg, 0.12 mmol) was reacted in accordance with the method for synthesizing the compound 6 to obtain N-α-[6-(2,3-di-tert-butoxycarbonylguanidino)hexyl]-L-3-(2-naphthyl)-alanyl-(O-tert-butyl)-L-tyrosyl-N-ε-(tert-butoxycarbonyl)-L-lysyl-L-tryptophanamide (compound 35; yield: 44 mg).

Step 4

N-α-6-Guanidinohexyl-L-3-(2-naphthyl)-alanyl-L-tyrosyl-L-lysyl-L-tryptophanamide (SEQ. ID. NO 3)

The compound 35 (44 mg, 0.04 mmol) was reacted in accordance with the method for synthesizing the compound 20 to obtain N-α-6-guanidinohexyl-L-3-(2-naphthyl)-alanyl-L-tyrosyl-L-lysyl-L-tryptophanamide (compound 36; yield: 25 mg).

FAB MS [M+H]$^+$=833

EXAMPLE 7

N-α-6-Guanidinohexyl-L-4,4'-biphenylalanyl-L-tyrosyl-L-lysyl-L-tryptophanamide (SEQ. ID. NO 3)

Step 1

N-α-9-Fluorenylmethoxycarbonyl-L-4,4'-biphenylalanyl-(O-tert-butyl)-L-tyrosyl-N-ε-(tert-butoxycarbonyl)-L-lysyl-L-tryptophanamide N-α-9-fluorenylmethoxycarbonyl-L-4,4'-biphenylalanine (178 mg, 0.38 mmol) was reacted in accordance with the method for synthesizing the compound 29 to obtain N-α-9-fluorenylmethoxycarbonyl-L-4,4'-biphenylalanyl-(O-tert-butyl)-L-tyrosyl-N-ε-(tert-butoxycarbonyl)-L-lysyl-L-tryptophanamide (compound 37; yield: 391 mg).

Step 2

L-4,4'-Biphenylalanyl-(O-tert-butyl)-L-tyrosyl-N-ε-(tert-butoxycarbonyl)-L-lysyl-L-tryptophanamide The compound 37 (380 mg, 0.35 mmol) was reacted in accordance with the method for synthesizing the compound 14 to obtain L-4,4'-biphenylalanyl-(O-tert-butyl)-L-tyrosyl-N-ε-(tert-butoxycarbonyl)-L-lysyl-L-tryptophanamide (compound 38; yield: 296 mg).

Step 3

N-α-[6-(2,3-di-tert-Butoxycarbonylguanidino)hexyl]-L-4,4'-biphenylalanyl-(O-tert-butyl)-L-tyrosyl-N-ε-(tert-butoxycarbonyl)-L-lysyl-L-tryptophanamide (SEQ. ID. NO 4)

The compound 38 (150 mg, 0.17 mmol) and a crude product of the compound 5 (102 mg, 0.29 mmol) were reacted in accordance with the method for synthesizing the compound 6 to obtain N-α-[6-(2,3-di-tert-butoxycarbonylguanidino)hexyl]-L-4,4'-biphenylalanyl-(O-tert-butyl)-L-tyrosyl-N-ε-(tert-butoxycarbonyl)-L-lysyl-L-tryptophanamide (compound 39; yield: 120 mg).

Step 4

N-α-6-Guanidinohexyl-L-4,4'-biphenylalanyl-L-tyrosyl-L-lysyl-L-tryptophanamide (SEQ. ID. NO 4)

The compound 39 (120 mg, 0.10 mmol) was reacted in accordance with the method for synthesizing the compound 20 to obtain N-α-6-guanidinohexyl-L-4,4'-biphenylalanyl-L-tyrosyl-L-lysyl-L-tryptophanamide (compound 40; yield: 78 mg).

FAB MS [M+H]$^+$=859

EXAMPLE 8

N-α-6-Guanidinohexyl-4-fluoro-L-phenylalanyl-L-tyrosyl-L-lysyl-L-tryptophanamide (SEQ. ID. NO 5)

Step 1

N-α-9-Fluorenylmethoxycarbonyl-4-fluoro-L-phenylalanyl-(O-tert-butyl)-L-tyrosyl-N-ε-(tert-butoxycarbonyl)-L-lysyl-L-tryptophanamide N-α-9-fluorenylmethoxycarbonyl-4-fluoro-L-phenylalanine (156 mg, 0.38 mmol) was reacted in accordance with the method for synthesizing the compound 29 to obtain N-α-9-fluorenylmethoxycarbonyl-4-fluoro-L-phenylalanyl-(O-tert-butyl)-L-tyrosyl-N-ε-(tert-butoxycarbonyl)-L-lysyl-L-tryptophanamide (compound 41; yield: 379 mg).

Step 2

4-Fluoro-L-phenylalanyl-(O-tert-butyl)-L-tyrosyl-N-ε-(tert-butoxycarbonyl)-L-lysyl-L-tryptophanamide The compound 41 (370 mg, 0.37 mmol) was reacted in accordance with the method for synthesizing the compound 14 to obtain 4-fluoro-L-phenylalanyl-(O-tert-butyl)-L-tyrosyl-N-ε-(tert-butoxycarbonyl)-L-lysyl-L-tryptophanamide (compound 42; yield: 280 mg).

Step 3

N-α-[6-(2,3-di-tert-Butoxycarbonylguanidino)hexyl]-4-fluoro-L-phenylalanyl-(O-tert-butyl)-L-tyrosyl-N-ε-(tert-butoxycarbonyl)-L-lysyl-L-tryptophanamide (SEQ. ID. NO 6)

The compound 42 (150 mg, 0.18 mmol) and a crude product of the compound 5 (102 mg, 0.29 mmol) were reacted in accordance with the method for synthesizing the compound 6 to obtain N-α-[6-(2,3-di-tert-butoxycarbonylguanidino)hexyl]-4-fluoro-L-phenylalanyl-(O-tert-butyl)-L-tyrosyl-N-ε-(tert-butoxycarbonyl)-L-lysyl-L-tryptophanamide (compound 43; yield: 122 mg).

Step 4

N-α-6-Guanidinohexyl-4-fluoro-L-phenylalanyl-L-tyrosyl-L-lysyl-L-tryptophanamide (SEQ. ID. NO 5)

The compound 43 (122 mg, 0.11 mmol) was reacted in accordance with the method for synthesizing the compound 20 to obtain N-α-6-guanidinohexyl-4-fluoro-L-phenylalanyl-L-tyrosyl-L-lysyl-L-tryptophanamide (compound 44; yield: 75 mg).

FAB MS $[M+H]^+$=801

EXAMPLE 9

N-α-6-guanidinohexyl-4-amino-L-phenylalanyl-L-tyrosyl-L-lysyl-L-tryptophanamide (SEQ. ID. NO 5)

Step 1

N-α-9-Fluorenylmethoxycarbonyl-4-amino-N-tert-butoxycarbonyl-L-phenylalanyl-(O-tert-butyl)-L-tyrosyl-N-ε-(tert-butoxycarbonyl)-L-lysyl-L-tryptophanamide N-α-9-fluorenylmethoxycarbonyl-4-amino-N-tert-butoxycarbonyl-L-phenylalanine (197 mg, 0.39 mmol) was reacted in accordance with the method for synthesizing the compound 29 to obtain N-α-9-fluorenylmethoxycarbonyl-4-amino-N-tert-butoxycarbonyl-L-phenylalanyl-(O-tert-butyl)-L-tyrosyl-N-ε-(tert-butoxycarbonyl)-L-lysyl-L-tryptophanamide (compound 45; yield: 416 mg).

Step 2

4-Amino-N-tert-butoxycarbonyl-L-phenylalanyl-(O-tert-butyl)-L-tyrosyl-N-ε-(tert-butoxycarbonyl)-L-lysyl-L-tryptophanamide The compound 45 (410 mg, 0.36 mmol) was reacted in accordance with the method for synthesizing the compound 14 to obtain 4-amino-N-tert-butoxycarbonyl-L-phenylalanyl-(O-tert-butyl)-L-tyrosyl-N-ε-(tert-butoxycarbonyl)-L-lysyl-L-tryptophanamide (compound 46; yield: 305 mg).

Step 3

N-α-[6-(2,3-di-tert-Butoxycarbonylguanidino)hexyl]-4-amino-N-tert-butoxycarbonyl-L-phenylalanyl-(O-tert-butyl)-L-tyrosyl-N-ε-(tert-butoxycarbonyl)-L-lysyl-L-tryptophanamide (SEQ. ID. NO 6)

The compound 46 (166 mg, 0.18 mmol) and a crude product of the compound 5 (98 mg, 0.27 mmol) were reacted in accordance with the method for synthesizing the compound 6 to obtain N-α-[6-(2,3-di-tert-butoxycarbonylguanidino)hexyl]-4-amino-N-tert-butoxycarbonyl-L-phenylalanyl-(O-tert-butyl)-L-tyrosyl-N-ε-(tert-butoxycarbonyl)-L-lysyl-L-tryptophanamide (compound 47; yield: 106 mg).

Step 4

N-α-6-Guanidinohexyl-4-amino-L-phenylalanyl-L-tyrosyl-L-lysyl-L-tryptophanamide (SEQ. ID. NO 5)

The compound 47 (106 mg, 0.08 mmol) was reacted in accordance with the method for synthesizing the compound 20 to obtain N-α-6-guanidinohexyl-4-amino-L-phenylalanyl-L-tyrosyl-L-lysyl-L-tryptophanamide (compound 48; yield: 55 mg).

FAB MS $[M+H]^+$=798

EXAMPLE 10

N-α-6-Guanidinohexyl-L-2-indanyl-glycyl-L-tyrosyl-L-lysyl-L-tryptophanamide (SEQ. ID. NO 7)

Step 1

N-α-9-fluorenylmethoxycarbonyl-L-2-indanyl-glycyl-(O-tert-butyl)-L-tyrosyl-N-ε-(tert-butoxycarbonyl)-L-lysyl-L-tryptophanamide N-α-9-fluorenylmethoxycarbonyl-L-2-indanyl-glycine (159 mg, 0.38 mmol) was reacted in accordance with the method for synthesizing the compound 29 to obtain N-α-9-fluorenylmethoxycarbonyl-L-2-indanyl-glycyl-(O-tert-butyl)-L-tyrosyl-N-ε-(tert-butoxycarbonyl)-L-lysyl-L-tryptophanamide (compound 49; yield: 405 mg).

Step 2

L-2-Indanyl-glycyl-(O-tert-butyl)-L-tyrosyl-N-ε-(tert-butoxycarbonyl)-L-lysyl-L-tryptophanamide The compound 49 (400 mg, 0.38 mmol) was reacted in accordance with the method for synthesizing the compound 14 to obtain L-2-indanyl-glycyl-(O-tert-butyl)-L-tyrosyl-N-ε-(tert-butoxycarbonyl)-L-lysyl-L-tryptophanamide (compound 50; yield: 281 mg).

Step 3

N-α-[6-(2,3-di-tert-Butoxycarbonylguanidino)hexyl]-L-2-indanyl-glycyl-(O-tert-butyl)-L-tyrosyl-N-ε-(tert-butoxycarbonyl)-L-lysyl-L-tryptophanamide (SEQ. ID. NO 8)

The compound 50 (150 mg, 0.18 mmol) and a crude product of the compound 5 (98 mg, 0.27 mmol) were reacted in accordance with the method for synthesizing the compound 6 to obtain N-α-[6-(2,3-di-tert-butoxycarbonylguanidino)hexyl]-L-2-indanyl-glycyl-(O-tert-butyl)-L-tyrosyl-N-ε-(tert-butoxycarbonyl)-L-lysyl-L-tryptophanamide (compound 51; yield: 93 mg).

Step 4

N-α-6-Guanidinohexyl-L-2-indanyl-glycyl-L-tyrosyl-L-lysyl L-tryptophanamide (SEQ. ID. NO 7)

The compound 51 (93 mg, 0.08 mmol) was reacted in accordance with the method for synthesizing the compound 20 to obtain N-α-6-guanidinohexyl-L-2-indanyl-glycyl-L-tyrosyl-L-lysyl-L-tryptophanamide (compound 52; yield: 57 mg).
FAB MS [M+H]$^+$=809

EXAMPLE 11

N-α-6-guanidinohexyl-L-tyrosyl-L-tyrosyl-L-lysyl-L-tryptophanol (SEQ. ID. NO 9)

Step 1

N-9-Fuorenylmethoxycarbonyl-N-ε-tert-butoxycarbonyl-lysine benzyl ester

N-9-Fluorenylmethoxycarbonyl-N-ε-tert-butoxycarbonyl-lysine (6.0 g, 12.8 mmol) and benzyl alcohol (1.6 mL, 15.5 mmol) was dissolved in methylene chloride (50 mL), cooled to 0° C., combined with dimethylaminopyridine (142 mg, 1.2 mmol) and 1-ethyl-3-(3-dimethylaminopropyl)carbodiimide hydrochloride (WSC; 2.7 g, 14.1 mmol), stirred at 0° C. for 2 hours, and further stirred at room temperature overnight. The reaction solution was extracted with chloroform, washed with a saturated aqueous solution of sodium hydrogen carbonate, saturated brine and water. The organic layer was dried over sodium sulfate, made free of solids by filtration through a cotton plug and washed with chloroform. The filtrate and the wash were combined and concentrated under reduced pressure, and the resultant residue was subjected to a column chromatography to obtain N-9-fluorenylmethoxycarbonyl-N-ε-tert-butoxycarbonyl-lysine benzyl ester (compound 53; yield: 7.1 g).

Step 2

N-ε-tert-Butoxycarbonyl-lysine benzyl ester

The compound 53 was reacted in accordance with the method for synthesizing the compound 14 to obtain N-ε-tert-butoxycarbonyl-lysine benzyl ester (compound 54; yield: 4.1 g).

Step 3

N-α-9-Fluorenylmethoxycarbonyl-O-tert-butyl-L-tyrosyl-N-ε-(tert-butoxycarbonyl)-L-lysine benzyl ester N-α-9-Fluorenylmethoxycarbonyl-O-tert-butyl-L-tyrosine (5.6 g, 12.2 mmol) was dissolved in DMF (65 mL), combined with 1-hydroxybenzotriazole (1.8 g, 13.3 mmol) and 1-ethyl-3-(3-dimethylaminopropyl)carbodiimide hydrochloride (WSC; 2.6 g, 13.4 mmol) and stirred at room temperature for 10 minutes. This was cooled to 0° C., combined with the compound 54 (4.1 g, 12.2 mmol) and stirred further at room temperature overnight. The reaction solution was extracted with ethyl acetate, washed with a saturated aqueous solution of sodium hydrogen carbonate, saturated brine and water. The organic layer was dried over sodium sulfate, made free of solids by filtration through a cotton plug, washed with ethyl acetate, and the filtrate and the wash were combined and concentrated under reduced pressure. The resultant reaction product was evaporated sufficiently into dryness under reduced pressure to obtain N-α-9-fluorenylmethoxycarbonyl-O-tert-butyl-L-tyrosyl-N-ε-tert-butoxycarbonyl-L-lysine benzyl ester (compound 55; yield: 9.4 g).

Step 4

O-tert-butyl-L-Tyrosyl-O-tert-butyl-L-tyrosyl-N-ε-tert-butoxycarbonyl-L-lysine benzyl ester The compound 55 (9.4 g, 12.1 mmol) was dissolved in DMF (80 mL) and cooled to 0° C. with stirring while cooling on ice. This was combined with piperidine (6.0 mL, 61 mmol), stirred further for 25 minutes, and then the reaction solution was poured into water, and extracted with ethyl acetate. The organic layer was washed with a 6% aqueous solution of potassium hydrogen sulfate, a saturated aqueous solution of sodium hydrogen carbonate, saturated brine and water. The organic layer was dried over sodium sulfate, made free of solids by filtration through a cotton plug, and washed with ethyl acetate. The filtrate and the wash were combined and concentrated under reduced pressure. The resultant residue was dissolved in DMF (20 mL), poured into a solution prepared previously by dissolving N-α-9-fluorenylmethoxycarbonyl-O-tert-butyl-L-tyrosine (5.6 g, 12.2 mmol) in DMF (65 mL), adding 1-hydroxybenzotriazole (1.8 g, 13.3 mmol) and 1-ethyl-3-(3-dimethylaminopropyl)carbodiimide hydrochloride (WSC; 2.6 g, 13.4 mmol), stirring at room temperature for 10 minutes and then cooling to 0° C., and then stirred further at room temperature overnight. The reaction solution was extracted with ethyl acetate, washed with a saturated aqueous solution of sodium hydrogen carbonate, saturated brine and water. The organic layer was dried over sodium sulfate, made free of solids by filtration through a cotton plug, and washed with ethyl acetate. The filtrate and the wash were combined and concentrated under reduced pressure. The resultant syrup was combined with a 10% piperidine/DMF solution (120 mL) and dissolved, and then stirred at room temperature for 20 minutes. The reaction solution was concentrated under reduced pressure, and the resultant residue was subjected to a column chromatography to obtain O-tert-butyl-L-tyrosyl-O-tert-butyl-L-tyrosyl-N-ε-tert-butoxycarbonyl-L-lysine benzyl ester (compound 56; yield: 8.6 g).

Step 5

N-α-[6-(2,3-di-tert-Butoxycarbonyl)guanidinohexyl]-O-tert-butyl-L-tyrosyl-O-tert-butyl-L-tyrosyl-N-ε-tert-butoxycarbonyl-L-lysine benzyl ester (SEQ. ID. NO 10)

The compound 56 (4 g, 5.2 mmol) and a crude product of the compound 5 (2.2 g, 6.1 mmol) were reacted in accordance with the method for synthesizing the compound 6 to obtain N-α-[6-(2,3-di-tert-butoxycarbonyl)guanidinohexyl]-O-tert-butyl-L-tyrosyl-O-tert-butyl-L-tyrosyl-(N-ε-tert-butoxycarbonyl)-L-lysine benzyl ester (compound 57; yield: 2.2 g).

Step 6

N-α-[6-(2,3-di-tert-Butoxycarbonyl)guanidinohexyl]-O-tert-butyl-L-tyrosyl-O-tert-butyl-L-tyrosyl-N-ε-tert-butoxycarbonyl-L-lysine (SEQ. ID. NO 10)

The compound 57 (2.2 g, 1.97 mmol) was dissolved in methanol (100 mL), combined with acetic acid (10 mL) and 10% Pd-C (500 mg), and stirred at room temperature for 5 hours. The reaction solution was filtered through Celite to remove solids, and washed with methanol. The filtrate and the wash were combined and concentrated under reduced pressure, and the resultant residue was combined with ethyl acetate and extracted, and the organic layer was washed with a saturated aqueous solution of sodium hydrogen carbonate, saturated brine and water. The organic layer was dried over sodium sulfate, made free of solids by filtration through a cotton plug, and washed with ethyl acetate. The filtrate and the wash were combined and concentrated under reduced pressure to obtain N-α-[6-(2,3-di-tert-butoxycarbonyl)guanidinohexyl]-O-tert-butyl-L-tyrosyl-O-tert-butyl-L-tyrosyl-(N-ε-tert-butoxycarbonyl)-L-lysine (compound 58; yield: 1.9 g).

Step 7

N-α-[6-(2,3-di-tert-Butoxycarbonyl)guanidinohexyl]-O-tert-butyl-L-tyrosyl-O-tert-butyl-L-tyrosyl-N-ε-tert-butoxycarbonyl-L-lysyl-L-tryptophanol (SEQ. ID. NO 10)

L-Tryptophanol (37 mg, 0.19 mmol) and the compound 58 (100 mg, 0.10 mmol) were dissolved in DMF (2 mL), combined with 1-hydroxybenzotriazole (15 mg, 0.11 mmol) and 1-ethyl-3-(3-dimethylaminopropyl)carbodiimide hydrochloride (WSC; 21 mg, 0.11 mmol) and stirred at room temperature overnight. The reaction solution was extracted with ethyl acetate, washed with a saturated aqueous solution of sodium hydrogen carbonate, saturated brine and water. The organic layer was dried over sodium sulfate, made free of solids by filtration through a cotton plug, washed with ethyl acetate, and the filtrate and the wash were combined and concentrated under reduced pressure. The resultant residue was subjected to a column chromatography to obtain N-α-[6-(2,3-di-tert-butoxycarbonyl)guanidinohexyl]-O-tert-butyl-L-tyrosyl-O-tert-butyl-L-tyrosyl-N-ε-tert-butoxycarbonyl-L-lysyl-L-tryptophanol (compound 59; yield: 106 mg).

Step 8

N-α-6-Guanidinohexyl-L-tyrosyl-L-tyrosyl-L-lysyl-L tryptophanol (SEQ. ID. NO 9)

The compound 59 (106 mg, 0.09 mmol) was reacted in accordance with the method for synthesizing the compound 20 to obtain N-α-6-guanidinohexyl-L-tyrosyl-L-tyrosyl-L-lysyl-L-tryptophanol (compound 60; yield: 45 mg).

FAB MS [M+H]$^+$=786

EXAMPLE 12

N-α-6-Guanidinohexyl-L-tyrosyl-L-tyrosyl-L-lysyl-L-phenylalaninol (SEQ. ID. NO 11)

Step 1

N-α-[6-(2,3-di-tert-Butoxycarbonyl)guanidinohexyl]-O-tert-butyl-L-tyrosyl-O-tert-butyl-L tyrosyl-N-ε-tert-butoxycarbonyl-L-lysyl-L-phenylalaninol (SEQ. ID. NO 12)

L-phenylalaninol (30 mg, 0.20 mmol) and the compound 58 (100 mg, 0.10 mmol) was reacted in accordance with the method for synthesizing the compound 59 to obtain N-α-[6-(2,3-di-tert-butoxycarbonyl)guanidinohexyl]-O-tert-butyl-L-tyrosyl-O-tert-butyl-L-tyrosyl-N-ε-tert-butoxycarbonyl-L-lysyl-L-phenylalaninol (compound 61; yield: 111 mg).

Step 2

N-α-6-Guanidinohexyl-L-tyrosyl-L-tyrosyl-L-lysyl-L-phenylalaninol (SEQ. ID. NO 11)

The compound 61 (111 mg, 0.10 mmol) was reacted in accordance with the method for synthesizing the compound 20 to obtain N-α-6-guanidinohexyl-L-tyrosyl-L-tyrosyl-L-lysyl-L-phenylalaninol (compound 62; yield: 57 mg).

FAB MS [M+H]$^+$=747

EXAMPLE 13

N-α-6-Guanidinohexyl-L-tyrosyl-L-tyrosyl-N-benzyl-N-(2-hydroxyethyl)-L-lysinamide Step 1

N-α-[6-(2,3-di-tert-Butoxycarbonyl)guanidinohexyl]-O-tert-butyl-L-tyrosyl-O-tert-butyl-L-tyrosyl-N-benzyl-N-(2-hydroxyethyl)-N-ε-tert-butoxycarbonyl-L-lysinamide N-Benzylethanolamine (35 mg, 0.23 mmol) and the compound 58 (120 mg, 0.12 mmol) were reacted in accordance with the method for synthesizing the compound 59 to obtain N-α-[6-(2,3-di-tert-butoxycarbonyl)guanidinohexyl]-O-tert-butyl-L-tyrosyl-O-tert-butyl-L-tyrosyl-N-benzyl-N-(2-hydroxyethyl)-N-ε-tert-butoxycarbonyl-L-lysinamide (compound 63; yield: 81 mg).

Step 2

N-α-6-Guanidinohexyl-L-tyrosyl-L-tyrosyl-N-benzyl-N-(2-hydroxyethyl)-L-lysinamide The compound 63 (81 mg, 0.07 mmol) was reacted in accordance with the method for synthesizing the compound 20 to obtain N-α-6-guanidinohexyl-L-tyrosyl-L-tyrosyl-N-benzyl-N-(2-hydroxyethyl)-N-ε-tert-butoxycarbonyl-L-lysinamide (compound 64; yield: 9.0 mg).
FAB MS [M+H]$^+$=747

EXAMPLE 14

N-α-6-guanidinohexyl-L-tyrosyl-L-tyrosyl-N-(1-naphthalenemethyl)-L-lysinamide

Step 1

N-α-[6-(2,3-di-tert-Butoxycarbonyl)guanidinohexyl]-O-tert-butyl-L-tyrosyl-O-tert-butyl-L-tyrosyl-N-(1-naphthalenemethyl)-N-ε-tert-butoxycarbonyl-L-lysinamide 1-Naphthalene methylamine (31 mg, 0.20 mmol) and the compound 58 (120 mg, 0.12 mmol) were reacted in accordance with the method for synthesizing the compound 59 to obtain N-α-[6-(2,3-di-tert-butoxycarbonyl)guanidinohexyl]-O-tert-butyl-L-tyrosyl-O-tert-butyl-L-tyrosyl-(N-1-naphthalenemethyl)-N-ε-tert-butoxycarbonyl-L-lysinamide (compound 65; yield: 101 mg).

Step 2

N-α-6-Guanidinohexyl-L-tyrosyl-L-tyrosyl-N-(1-naphthalenemethyl)-L-lysinamide

The compound 20 (101 mg, 0.09 mmol) was reacted in accordance with the method for synthesizing the compound 60 to obtain N-α-6-guanidinohexyl-L-tyrosyl-L-tyrosyl-(N-1-naphthalenemethyl)-L-lysinamide (compound 66; yield: 63 mg).
FAB MS [M+H]$^+$=753

EXAMPLE 15

N-α-6-Guanidinohexyl-D-tyrosyl-L-tyrosyl-L-lysyl-L-tryptophanamide (SEQ. ID. NO 9)

Step 1

O-tert-Butyl-D-tyrosyL-O-tert-butyl-L-tyrosyl-N-ε-tert-butoxycarbonyl-L-lysyl-L-tryptophanamide (SEQ. ID. NO 9)

N-α-9-Fluorenylmethoxycarbonyl-O-tert-butyl-D-tyrosine (206 mg, 0.45 mmol) and the compound 28 (300 mg, 0.46 mmol) were reacted in accordance with the method for synthesizing the compound 1 to obtain (O-tert-butyl)-D-tyrosyl-(O-tert-butyl)-L-tyrosyl-(N-ε-tert-butoxycarbonyl)-L-lysyl-L-tryptophanamide (compound 67; yield: 362 mg).

Step 2

N-α-[6-(2,3-di-tert-Butoxycarbonyl)guanidinohexyl]-(O-tert-butyl)-D-tyrosyl-(O-tert-butyl)-L-tyrosyl-N-ε-tert-butoxycarbonyl-L-lysyl-L-tryptophanamide (SEQ. ID. NO 10)

A crude product of the compound 5 (83.3 mg) and the compound 67 (150 mg, 0.17 mmol) were reacted in accordance with the method for synthesizing the compound 6 to obtain N-α-[6-(2,3-di-tert-butoxycarbonyl)guanidinohexyl]-O-tert-butyl-D-tyrosyl-O-tert-butyl-L-tyrosyl-N-ε-tert-butoxycarbonyl-L-lysyl-L-tryptophanamide (compound 68; yield: 124 mg).

Step 3

N-α-6-guanidinohexyl-D-tyrosyl-L-tyrosyl-L-lysyl-L-tryptophanamide (SEQ. ID. NO 9)

The compound 68 (124 mg, 0.10 mmol) was reacted in accordance with the method for synthesizing the compound 20 to obtain N-α-6-guanidinohexyl-D-tyrosyl-L-tyrosyl-L-lysyl-L-tryptophanamide (compound 69; yield: 51.1 mg).
FAB MS [M+H]$^+$=799

EXAMPLE 16

N-α-6-Guanidinohexyl-N-methyl-L-tyrosyl-L-tyrosyl-L-lysyl-L-tryptophanamide (SEQ. ID. NO 9)

Step 1

N-α-[6-(2,3-di-tert-Butoxycarbonyl)guanidinohexyl]-O-tert-butyl-L-tyrosine benzyl ester A crude product of the compound 5 (2.4 g) and O-tert-butyl-L-tyrosine benzyl ester (1.78 g, 5.4 mmol) were reacted in accordance with the method for synthesizing the compound 6 to obtain N-α-[6-(2,3-di-tert-butoxycarbonyl)guanidinohexyl]-O-tert-butyl-L-tyrosine benzyl ester (compound 70; yield: 1.32 g).

Step 2

N-α-[6-(2,3-di-tert-Butoxycarbonyl)guanidino-hexyl]-N-methyl-O-tert-butyl-L-tyrosine benzyl ester The compound 70 (260 mg, 0.39 mmol) was dissolved in a mixture of methanol (2.7 mL) and formaldehyde solution (2.7 mL), adjusted at pH4 with acetic acid, and then combined with sodium cyanoborohydride (54.0 mg, 0.86 mmol) and stirred at room temperature for 30 minutes. After completion of the reaction, the reaction solution was concentrated under reduced pressure, and the resultant residue was extracted with ethyl acetate, and the organic layer was washed with a saturated aqueous solution of sodium hydrogen carbonate, saturated brine and water. The organic layer was dried over sodium sulfate, made free of solids by filtration through a cotton plug, and washed with ethyl acetate. The filtrate and the wash were combined and concentrated under reduced pressure, and the resultant residue was subjected to a column chromatography to obtain N-α-[6-(2,3-di-tert-butoxycarbonyl)guanidinohexyl]-N-methyl-O-tert-butyl-L-tyrosine benzyl ester (compound 71; yield: 197 mg).

Step 3

N-α-[6-(2,3-di-tert-Butoxycarbonylguanidino)hexyl]-N-methyl-O-tert-butyl-L-tyrosine The compound 71 (197 mg, 0.29 mmol) was reacted in accordance with the method for synthesizing compound 58 to obtain N-α-[6-(2,3-di-tert-butoxycarbonylguanidino)hexyl]-N-methyl-(O-tert-butyl)-L-tyrosine (compound 72; yield: 164 mg).

Step 4

N-α-[6-(2,3-di-tert-Butoxycarbonylguanidino)hexyl]-N-methyl-O-tert-butyl-L-tyrosyl-O-tert butyl-L-tyrosyl-N-ε-tert-butoxycarbonyl-L-lysyl-L-tryptophanamide (SEQ. ID. NO 10)

The compound 72 (88.7 mg, 0.15 mmol) and the compound 28 (97.4 mg, 0.15 mmol) were dissolved in DMF (3 mL), combined with WSC (31.6 mg, 0.16 mmol) and 1-hydroxybenzotriazole (22.2 mg, 0.16 mmol) and stirred overnight. The reaction solution was extracted with ethyl acetate, washed with a saturated aqueous solution of sodium hydrogen carbonate, saturated brine and water. The organic layer was dried over sodium sulfate, made free of solids by filtration through a cotton plug, and washed with ethyl acetate. The filtrate and the wash were combined and concentrated under reduced pressure, and the resultant residue was subjected to a column chromatography to obtain N-α-[6-(2,3-di-tert-butoxycarbonylguanidino)hexyl]-N-methyl-O-tert-butyl-L-tyrosyl-O-tert-butyl-L-tyrosyl-N-ε-tert-butoxycarbonyl-L-lysyl-L-tryptophanamide (compound 73; yield: 115 mg).

Step 5

N-α-6-Guanidinohexyl-N-methyl-L-tyrosyl-L-tyrosyl-L-lysyl-L-tryptophanamide (SEQ. ID. NO 9)

The compound 73 (115 mg, 0.09 mmol) was reacted in accordance with the method for synthesizing the compound 20 to obtain N-α-6-guanidinohexyl-N-methyl-L-tyrosyl-L-tyrosyl-L-lysyl-L-tryptophanamide (compound 74; yield: 65.2 mg).

FAB MS $[M+H]^+$=813

EXAMPLE 17

N-α-6-Guanidinohexyl-L-tyrosyl-L-tyrosyl-N-[(R)-1-(2-naphthyl)ethyl]-L-lysinamide Step 1

N-α-[6-(2,3-di-tert-Butoxycarbonyl)guanidino-hexyl]-O-tert-butyl-L-tyrosyl-O-tert-butyl-L-tyrosyl-N-[(R)-1-(2-naphthyl) ethyl]-N-ε-tert-butoxycarbonyl-L-lysinamide R-(+)-1-(2-Naphthyl)ethylamine (33.4 mg, 0.20 mmol) and the compound 58 (100 mg, 0.10 mmol) were reacted in accordance with the method for synthesizing the compound 59 to obtain N-α-[6-(2,3-di-tert-butoxycarbonyl)guanidino-hexyl]-O-tert-butyl-L-tyrosyl-O-tert-butyl-L-tyrosyl-N-[(R)-1-(2-naphthyl)ethyl]-N-ε-tert-butoxycarbonyl-L-lysinamide (compound 75; yield: 78.3 mg).

Step 2

N-α-6-Guanidinohexyl-L-tyrosyl-L-tyrosyl-N-[(R)-1-(2-naphthyl)ethyl]-L-lysinamide The compound 75 (78.3 mg, 0.07 mmol) was reacted in accordance with the method for synthesizing the compound 20 to obtain N-α-6-guanidinohexyl-L-tyrosyl-L-tyrosyl-N-[(R)-1-(2-naphthyl)ethyl]-L-lysinamide (compound 76; yield: 50 mg).

FAB MS $[M+H]^+$=767

EXAMPLE 18

N-α-[(S)-2-N'-[N''-6-Guanidinohexyl-L-tyrosyl]amino-3-(4-hydroxy)phenyl]propyl-L-lysyl-L-tryptophanamide Step 1

N-α-[3-(4-O-tert-Butyl)phenyl-(S)-2-N-(9-fluorenylmethoxycarbonyl)amino]-propyl-N-ε-tert-butoxycarbonyl-L-lysyl-L-tryptophanamide N-α-9-Fluorenylmethoxycarbonyl-O-tert-butyl-L-tyrosinol (929 mg, 2.09 mmol) was dissolved in methylene chloride (20 mL), combined with Dess-Martin reagent (3.1 g, 7.3 mmol) and stirred for 10 minutes. After completion of the solution, the reaction solution was combined with a saturated aqueous solution of sodium hydrogen carbonate and an aqueous solution of sodium thiosulfate, stirred for 10 minutes, and extracted with ether. The organic layer was dried over sodium sulfate, made free of solids by filtration through a cotton plug, and then washed with ether. The filtrate and the wash were combined and concentrated under reduced pressure to obtain a crude product of N-α-9-fluorenylmethoxycarbonyl-O-tert-butyl-L-tyrosinal. This crude product and the compound 27 (600 mg, 1.39 mmol) were dissolved in methanol (5 mL), adjusted at pH4 with acetic acid, and then stirred at room temperature for 15 minutes. The reaction solution was cooled to 0° C., combined with sodium cyanoborohydride (393 mg, 6.25 mmol) and stirred at room temperature for 15 minutes. After completion of the reaction, the reaction solution was concentrated under reduced pressure, and the resultant residue was extracted with ethyl acetate, and the organic layer was washed with a saturated aqueous solution of sodium hydrogen carbonate, saturated brine and water. The organic layer was dried over sodium sulfate, made free of solids by filtration through a cotton plug, and washed with ethyl acetate. The filtrate and the wash were combined and concentrated under reduced pressure, and the resultant residue was subjected to a column chromatography to obtain N-α-[3-(4-O-tert-butyl)phenyl-(S)-2-N-(9-fluorenylmethoxycarbonyl)amino]-propyl-N-ε-tert-butoxycarbonyl-L-lysyl-L-tryptophanamide (compound 77; yield: 872.5 mg).

Step 2

N-α-[(S)-2-Amino-3-(4-O-tert-butyl)phenyl]propyl-N-ε-tert-butoxycarbonyl-L-lysyl-L-tryptophanamide The compound 77 (400 mg, 46.6 mmol) was reacted in accordance with the method for synthesizing the compound 14 to obtain N-α-[(S)-2-amino-3-(4-O-tert-butyl)phenyl] propyl-N-ε-tert-butoxycarbonyl-L-lysyl-L-tryptophanamide (compound 78; yield: 294 mg).

Step 3

N-α-[6-(2,3-di-tert-butoxycarbonyl)guanidinohexyl]-O-tert-butyl-L-tyrosine

The compound 70 (600 mg, 0.90 mmol) was reacted in accordance with the method for synthesizing the compound 58 to obtain N-α-[6-(2,3-di-tert-butoxycarbonyl)guanidinohexyl]-O-tert-butyl-L-tyrosine (compound 79; yield: 483 mg).

Step 4

N-α-[(S)-2-N'-[N-α-{6-(2,3-di-tert-Butoxycarbonyl) guanidinohexyl}-O-tert-butyl-L-tyrosyl]amino-3-(4-O-tert-butyl)phenyl]propyl-N-ε-tert-butoxycarbonyl-L-lysyl-L-tryptophanamide The compound 78 (66.0 mg, 0.10 mmol) and the compound 79 (60.0 mg, 0.10 mmol) were reacted in accordance with the method for synthesizing the compound 73 to obtain N-α-[(S)-2-N'-[N-α-{6-(2,3-di-tert-butoxycarbonyl) guanidinohexyl}-O-tert-butyl-L-tyrosyl]amino-3-(4-O-tert-butyl) phenyl]propyl-N-ε-tert-butoxycarbonyl-L-lysyl-L-tryptophanamide (compound 80; yield: 92.6 mg).

Step 5

N-α-[(S)-2-N'-{N-α-6-guanidinohexyl-L-tyrosyl}amino-3-(4-hydroxy)phenyl]propyl-L-lysyl-L-tryptophanamide The compound 80 (92.6 mg, 0.08 mmol) was reacted in accordance with the method for synthesizing the compound 20 to obtain N-α-[(S)-2-N'-[N'''-6-guanidinohexyl-L-tyrosyl]amino-3-(4-hydroxy)phenyl]propyl-L-lysyl-L-tryptophanamide (compound 81; yield: 45.2 mg).
FAB MS [M+H]$^+$=785

EXAMPLE 19

N-α-6-Guanidinohexyl-L-tyrosyl-L-tyrosyl-N-[(R)-1-(2-naphthyl)ethyl]-L-argininamide Step 1

N-[(R)-1-(2-Napthyl) ethyl]-N-ω-(2,2,5,7,8-pentamethylchroman-6-sulfonyl)-L-argininamide N-α-9-Fluorenylmethoxycarbonyl-N-ω-(2,2,5,7,8-pentamethylchroman-6-sulfonyl)-L-arginine (3.0 g, 4.53 mmol) and R-(+)-1-(2-naphthyl)ethylamine (775 mg, 4.53 mmol) were reacted in accordance with the method for synthesizing the compound 1 to obtain N-[(R)-1-(2-naphthyl)ethyl]-N-ω-(2,2,5,7,8-pentamethylchroman-6-sulfonyl)-L-argininamide (compound 82; yield: 2.52 g).

Step 2

O-tert-Butyl-L-tyrosyl-N-[(R)-1-(2-naphthyl) ethyl]-N-ω-(2,2,5,7,8-pentamethylchroman-6-sulfonyl)-L-argininamide N-α-9-Fluorenylmethoxycarbonyl-O-tert-butyl-L-tyrosine (310 mg, 0.67 mmol) and the compound 82 (400 mg, 0.67 mmol) were reacted in accordance with the method for synthesizing the compound 1 to obtain O-tert-butyl-L-tyrosyl-N-[(R)-1-(2-naphthyl)ethyl]-N-ω-(2,2,5,7,8-pentamethylchroman-6-sulfonyl)-L-argininamide (compound 83; yield: 509 mg).

Step 3

N-α-[6-(2,3-di-tert-Butoxycarbonyl) guanidinohexyl]-O-tert-butyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide The compound 79 (55.0 mg, 0.10 mmol) and the compound 83 (77.2 mg, 0.10 mmol) were reacted in accordance with the method for synthesizing the compound 73 to obtain N-α-[6-(2,3-di-tert-butoxycarbonyl)guanidinohexyl]-O-tert-butyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide (compound 84; yield: 108 mg).

Step 4

N-α-6-Guanidinohexyl-L-tyrosyl-L-tyrosyl-N-[(R)-1-(2-naphthyl)ethyl]-L-argininamide The compound 84 (108 mg, 0.08 mmol) was reacted in accordance with the method for synthesizing the compound 7 to obtain N-α-6-guanidinohexyl-L-tyrosyl-L-tyrosyl-[N-(R)-1-(2-naphthyl)ethyl]-L-argininamide (compound 85; yield: 54.7 mg).
FAB MS [M+H]$^+$=795

EXAMPLE 20

N-α-6-guanidinohexyl-L-tyrosyl-L-3-(2-naphthyl)-alanyl-N-[(R)-1-(2-naphthyl)ethyl]-L-argininamide Step 1

L-3-(2-Naphthyl)-alanyl-N-[(R)-1-(2-naphthyl)ethyl]-N-ω-(2,2,5,7,8-pentamethylchroman-6-sulfonyl)-L-argininamide N-α-9-Fluorenylmethoxycarbonyl-L-3-(2-naphthyl)-alanine (295 mg, 0.67 mmol) and the compound 82 (400 mg, 0.67 mmol) were reacted in accordance with the method for synthesizing the compound 1 to obtain L-3-(2-naphthyl)-alanyl-[N-(R)-1-(2-naphthyl) ethyl]-(N-ω-2,2,5,7,8-pentamethylchroman-6-sulfonyl)-L-argininamide (compound 86; yield: 500 mg).

Step 2

N-α-[6-(2,3-di-tert-Butoxycarbonylguanidino)hexyl]-O-tert-butyl-L-tyrosyl-L-3-(2-naphthyl)-alanyl-N-[(R)-1-(2-naphthyl)ethyl]-N-ω-(2,2,5,7,8-pentamethylchroman-6-sulfonyl)-L-argininamide The compound 79 (61.1 mg, 0.11 mmol) and the compound 86 (83.5 mg, 0.11 mmol) were reacted in accordance with the method for synthesizing the compound 73 to obtain N-α-[6-(2,3-di-tert-butoxycarbonylguanidino)hexyl]-(O-tert-butyl)-L-tyrosyl-L-3-(2-naphthyl)-alanyl-[N-(R)-1-(2-naphthyl)ethyl]-(N-ω-2,2,5,7,8-pentamethylchroman-6-sulfonyl)-L-argininamide (compound 87; yield: 114 mg).

Step 3

N-α-6-Guanidinohexyl-L-tyrosyl-L-3-(2-naphthyl)-alanyl-N-[(R)-1-(2-naphthyl)ethyl]-L-argininamide The compound 87 (114 mg, 0.08 mmol) was reacted in accordance with the method for synthesizing the compound 7 to obtain N-α-6-guanidinohexyl-L-tyrosyl-L-3-(2-naphthyl)-alanyl-[N-(R)-1-(2-naphthyl)ethyl]-L-argininamide (compound 88; yield: 72.2 mg).

FAB MS [M+H]$^+$=829

EXAMPLE 21

N-α-6-Guanidinohexyl-L-3-(1-naphthyl)-alanyl-L-tyrosyl-N-[(R)-1-(2-naphthyl)ethyl]-L-argininamide Step 1

L-3-(1-Naphthyl)-alanyl-O-tert-butyl-L-tyrosyl-N-[(R)-1-(2-naphthyl)ethyl]-N-ω-(2,2,5,7,8-pentamethylchroman-6-sulfonyl)-L-argininamide N-α-9-Fluorenylmethoxycarbonyl-L-3-(1-naphthyl)-alanine (161 mg, 0.37 mmol) and the compound 83 (300 mg, 0.37 mmol) were reacted in accordance with the method for synthesizing the compound 1 to obtain L-3-(1-naphthyl)-alanyl-O-tert-butyl-L-tyrosyl-N-[(R)-1-(2-naphthyl)ethyl]-N-ω-(2,2,5,7,8-pentamethylchroman-6-sulfonyl)-L-argininamide (compound 89; yield: 365 mg).

Step 2

N-α-[6-(2,3-di-tert-Butoxycarbonyl)guanidinohexyl]-L-3-(1-naphthyl)-alanyl-O-tert-butyl-L-tyrosyl-N-[(R)-1-(2-naphthyl)ethyl]-N-ω-(2,2,5,7,8-pentamethylchroman-6-sulfonyl)-L-argininamide A crude product of the compound 5 (63 mg) and the compound 89 (150 mg, 0.15 mmol) were reacted in accordance with the method for synthesizing the compound 6 to obtain N-α-[6-(2,3-di-tert-butoxycarbonyl)guanidinohexyl]-L-3-(1-naphthyl)-alanyl-(O-tert-butyl)-L-tyrosyl-[N-(R)-1-(2-naphthyl)ethyl]-N-ω-(2,2,5,7,8-pentamethylchroman-6-sulfonyl)-L-argininamide (compound 90; yield: 101 mg).

Step 3

N-α-6-Guanidinohexyl-L-3-(1-naphthyl)-alanyl-L-tyrosyl-N-[(R)-1-(2-naphthyl)ethyl]-L-argininamide The compound 90 (101 mg, 0.08 mmol) was reacted in accordance with the method for synthesizing the compound 7 to obtain N-α-6-guanidinohexyl-L-3-(1-naphthyl)-alanyl-L-tyrosyl-N-[(R)-1-(2-naphthyl)ethyl]-L-argininamide (compound 91; yield: 56.6 mg).

FAB MS [M+H]$^+$=829

EXAMPLE 22

N-α-4-Guanidinobutylcarbamoyl-L-tyrosyl-L-tyrosyl-N-[(R)-1-(2-naphthyl)ethyl]-L-argininamide Step 1

4-(2,3-di-tert-Butoxycarbonyl)guanidino-1-butylamine 1,4-Di-aminobutane (1.37 g, 15.5 mmol) was dissolved in methylene chloride (30 mL), combined with 1,3-bis(tert-butoxycarbonyl)-2-methyl-2-thiopseudourea (1.50 g, 5.17 mmol) and stirred overnight. The reaction solution was concentrated under reduced pressure, and the residue was subjected to a column chromatography to obtain 4-(2,3-di-tert-butoxycarbonyl)guanidino-1-butylamine (compound 92; yield: 813 mg).

Step 2

N-α-[4-(2,3-di-tert-Butoxycarbonyl)guanidinobutylcarbamoyl]-O-tert-butyl-L-tyrosine benzyl ester Triphosgene (84.0 mg, 0.28 mmol) was dissolved in methylene chloride, combined under argon flow with O-tert-butyl-L-tyrosine benzyl ester (250 mg, 0.76 mg) and N,N-diisopropylethylamine (146 μM 0.84 mmol) and stirred at room temperature for 2.5 minutes. This reaction solution was combined with the compound 92 (278 mg, 0.84 mmol) and N,N-diisopropylethylamine (161 μL, 0.92 mmol) dissolved in methylene chloride (2 mL), and stirred at room temperature further for 10 minutes. After completion of the reaction, the mixture was extracted with ethyl acetate, and washed with a 6% aqueous solution of potassium sulfate, a saturated aqueous solution of sodium hydrogen carbonate, a saturated brine and water. The organic layer was dried over sodium sulfate, made free of solids by filtration through a cotton plug, and washed with ethyl acetate. The filtrate and the wash were combined and concentrated under reduced pressure. The resultant residue was subjected to a column chromatography to obtain N-α-[4-(2,3-di-tert-butoxycarbonyl)guanidinobutylcarbamoyl]-O-tert-butyl-L-tyrosine benzyl ester (compound 93; yield: 105 mg).

Step 3

N-α-[4-(2,3-di-tert-Butoxycarbonyl)guanidinobutylcarbamoyl]-O-tert-butyl-L-tyrosine The compound 93 (105 mg, 0.15 mmol) was reacted in accordance with the method for synthesizing the compound 58 to obtain N-α-[4-(2,3-di-tert-butoxycarbonyl)guanidinobutylcarbamoyl]-(O-tert-butyl)-L-tyrosine (compound 94; yield: 90.1 mg).

Step 4

N-α-[4-(2,3-di-tert-Butoxycarbonyl)quanidinobutylcarbamoyl]-O-tert-butyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide The compound 83 (123 mg, 0.15 mmol) and the compound 94 (90.1 mg, 0.15 mmol) were reacted in accordance with the method for synthesizing the compound 73 to obtain N-α-[4-(2,3-di-tert-butoxycarbonyl)guanidinobutylcarbamoyl]-O-tert-butyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide (compound 95; yield: 157 mg).

Step 5

N-α-4-Guanidinobutylcarbamoyl-L-tyrosyl-L-tyrosyl-N-[(R)-1-(2-naphthyl)ethyl]-L-argininamide The compound 95 (157 mg, 0.11 mmol) was reacted in accordance with the method for synthesizing the compound 7 to obtain N-α-4-guanidinobutylcarbamoyl-L-tyrosyl-L-tyrosyl-N-[(R)-1-(2-naphthyl)ethyl]-L-argininamide (compound 96; yield: 79.0 mg).

FAB MS [M+H]⁺=810

EXAMPLE 23

N-α-6-Guanidinopentyl-L-tyrosyl-L-tyrosyl-N-[(R)-1-(2-naphthyl)ethyl]-L-argininamide Step 1

6-(2,3-di-tert-Butoxycarbonyl)guanidino-1-pentanol

5-Amino-1-pentanol (1.00 g, 9.7 mmol) was reacted in accordance with the method for synthesizing the compound 4 to obtain 6-(2,3-di-tert-butoxycarbonyl)guanidino-1-pentanol (compound 97; yield: 3.21 mg).

Step 2

6-(2,3-di-tert-Butoxycarbonyl)guanidino-1-pentanal

The compound 97 (100 mg, 0.29 mmol) was reacted in accordance with the method for synthesizing the compound 5 to obtain a crude product of 6-(2,3-di-tert-butoxycarbonyl)guanidino-1-pentanal (compound 98) (95.0 mg).

Step 3

O-tert-Butyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide N-α-9-Fluorenylmethoxycarbonyl-O-tert-butyl-L-tyrosine (226 mg, 0.49 mmol) and the compound 83 (400 mg, 0.49 mmol) were reacted in accordance with the method for synthesizing the compound 1 to obtain O-tert-butyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide (compound 99; yield: 495 mg).

Step 4

N-α-[6-(2,3-di-tert-Butoxycarbonylguanidino)pentyl]-O-tert-butyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide A crude product of the compound 98 (95 mg) and the compound 99 (150 mg, 0.15 mmol) were reacted in accordance with the method for synthesizing the compound 6 to obtain N-α-[6-(2,3-di-tert-butoxycarbonylguanidino)pentyl]-O-tert-butyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide (compound 100; yield: 101 mg).

Step 5

N-α-6-Guanidinopentyl-L-tyrosyl-L-tyrosyl-N-[(R)-1-(2-naphthyl)ethyl]-L-argininamide The compound 100 (101 mg, 0.07 mmol) was reacted in accordance with the method for synthesizing the compound 7 to obtain N-α-6-guanidinopentyl-L-tyrosyl-L-tyrosyl-N-[(R)-1-(2-naphthyl)ethyl]-L-argininamide (compound 101; yield: 57.2 mg).

FAB MS [M+H]⁺=781

EXAMPLE 24

N-α-5-Guanidinopentylyl-L-tyrosyl-L-tyrosyl-L-arginyl-L-tryptophanamide

Step 1

5-Amino-n-valeric acid methyl ester

Methanol (15 mL) was cooled to 0° C., combined with thionyl chloride (1.25 mL, 17.1 mmol) and stirred further for 30 minutes. This reaction solution was combined with 5-amino-n-valeric acid (500 mg, 4.3 mmol) and stirred at room temperature overnight. After completion of the reaction, the mixture was concentrated under reduced pressure to obtain a residue, which was dissolved in methylene chloride (10 mL), combined with 1,3-bis(tert-butoxycarbonyl)-2-methyl-2-thiopseudourea (1.85 g, 6.4 mmol) and stirred overnight. The reaction solution was concentrated under reduced pressure, and the residue was subjected to a column chromatography to obtain 5-amino-n-valeric acid methyl ester (compound 102; yield: 865 mg).

Step 2

5-(2,3-di-tert-Butoxycarbonyl)guanidinovaleric acid

The compound 102 (865 mg, 2.32 mmol) was dissolved in a mixture of tetrahydrofuran (7 mL), methanol (3 mL) and water (2 mL), combined with lithium hydroxide monohydrate (300 mg, 7.15 mmol) and stirred at room temperature for 30 minutes. After completion of the reaction, the mixture was concentrated under reduced pressure and the resultant residue was extracted with ethyl acetate, and washed with a 6% aqueous solution of potassium hydrogen sulfate, a saturated brine and water. The organic layer was dried over sodium sulfate, made free of solids by filtration through a cotton plug, and washed with ethyl acetate. The filtrate and the wash were combined and concentrated under reduced pressure to obtain 5-(2,3-di-tert-butoxycarbonyl)guanidinovaleric acid (compound 103; yield: 826 mg).

Step 3

N-α-[5-(2,3-di-tert-Butoxycarbonyl)guanidinopentylyl]-O-tert-butyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide The compound 99 (115 mg, 0.11 mmol) and the compound 103 (52 mg, 0.15 mmol) were reacted in accordance with the method for synthesizing the compound 73 to obtain N-α-[5-(2,3-di-tert-butoxycarbonyl)guanidinopentylyl]-O-tert-butyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide (compound 104; yield: 81.2 mg).

Step 4

N-α-5-Guanidinopentylyl-L-tyrosyl-L-tyrosyl-L-arginyl-L-tryptophanamide

The compound 104 (81.2 mg, 0.06 mmol) was reacted in accordance with the method for synthesizing the compound 7 to obtain N-α-5-guanidinopentylyl-L-tyrosyl-L-tyrosyl-L-arginyl-L-tryptophanamide (compound 105; yield: 41.3 mg).

FAB MS $[M+H]^+=781$

EXAMPLE 25

N-α-6-Guanidinohexyl-3,5-dimethyl-L-tyrosyl-L-tyrosyl-N-[(R)-1-(2-naphthyl)ethyl]-L-argininamide Step 1

3,5-Dimethyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide N-α-9-Fluorenylmethoxycarbonyl-3,5-dimethyl-L-tyrosine (160 mg, 0.37 mmol) and the compound 83 (300 mg, 0.37 mmol) were reacted in accordance with the method for synthesizing the compound 1 to obtain 3,5-dimethyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide (compound 106; yield: 350 mg).

Step 2

N-α-[6-(2,3-di-tert-Butoxycarbonyl)guanidinohexyl]-3,5-dimethyl-L-tyrosyl-O-tert-butyl-L-tyrosyl-N-[(R)-1-(2-naphthyl)ethyl]-N-ω-(2,2,5,7,8-pentamethylchroman-6-sulfonyl)-L-argininamide A crude product of the compound 5 (89 mg) and the compound 106 (150 mg, 0.15 mmol) were reacted in accordance with the method for synthesizing the compound 6 to obtain N-α-[6-(2,3-di-tert-butoxycarbonyl)guanidinohexyl]-3,5-dimethyl-L-tyrosyl-O-tert-butyl-L-tyrosyl-AT-[(R)-1-(2-naphthyl)ethyl]-N-ω-(2,2,5,7,8-pentamethylchroman-6-sulfonyl)-L-argininamide (compound 107; yield: 87.2 mg).

Step 3

N-α-6-Guanidinohexyl-3,5-dimethyl-L-tyrosyl-L-tyrosyl-N-[(R)-1-(2-naphthyl)ethyl]-L-argininamide The compound 107 (87.2 mg, 0.06 mmol) was reacted in accordance with the method for synthesizing the compound 7 to obtain N-α-6-guanidinohexyl-3,5-dimethyl-L-tyrosyl-L-tyrosyl-N [(R)-1-(2-naphthyl)ethyl]-L-argininamide (compound 108; yield: 53.1 mg).

FAB MS $[M+H]^+=823$

EXAMPLE 26

N-α-6-Guanidinohexyl-L-tyrosyl-3,5-dimethyl-L-tyrosyl-N-[(R)-1-(2-naphthyl)ethyl]-L-argininamide Step 1

3,5-Dimethyl-L-tyrosyl-N-[(R)-1-(2-naphthyl)ethyl]-N-ω-(2,2,5,7,8-pentamethylchroman-6-sulfonyl)-L-argininamide N-α-9-Fluorenylmethoxycarbonyl-3,5-dimethyl-L-tyrosine (200 mg, 0.46 mmol) and the compound 82 (275 mg, 0.46 mmol) were reacted in accordance with the method for synthesizing the compound 1 to obtain 3,5-dimethyl-L-tyrosyl-N-[(R)-1-(2-naphthyl)ethyl]-N-ω-(2,2,5,7,8-pentamethylchroman-6-sulfonyl)-L-argininamide (compound 109; yield: 354 mg).

Step 2

O-tert-Butyl-L-tyrosyl-3,5-dimethyl-L-tyrosyl-N-[(R)-1-(2-naphthyl)ethyl]-N-ω-(2,2,5,7,8-pentamethylchroman-6-sulfonyl)-L-argininamide N-α-9-Fluorenylmethoxycarbonyl-O-tert-butyl-L-tyrosine (95 mg, 0.21 mmol) and the compound 109 (162 mg, 0.21 mmol) were reacted in accordance with the method for synthesizing the compound 1 to obtain O-tert-butyl-L-tyrosyl-3,5-dimethyl-L-tyrosyl-N-[(R)-1-(2-naphthyl)ethyl]-N-ω-(2,2,5,7,8-pentamethylchroman-6-sulfonyl)-L-argininamide (compound 110; yield: 196 mg).

Step 3

N-α-[6-(2,3-di-tert-Butoxycarbonyl)guanidinohexyl]-O-tert-butyl)-L-tyrosyl-3,5-dimethyl-L-tyrosyl-N-[(R)-1-(2-naphthyl)ethyl]-N-ω-(2,2,5,7,8-pentamethylchroman-6-sulfonyl)-L-argininamide A crude product of the compound 5 (124 mg) and the compound 110 (192 mg, 0.19 mmol) were reacted in accordance with the method for synthesizing the compound 6 to obtain N-α-[6-(2,3-di-tert-butoxycarbonyl)guanidinohexyl]-O-tert-butyl-L-tyrosyl-3,5-dimethyl-L-tyrosyl-N-[(R)-1-(2-naphtyl)ethyl]-N-ω-(2,2,5,7,8-pentamethylchroman-6-sulfonyl)-L-argininamide (compound 111; yield: 184 mg).

Step 4

N-α-6-Guanidinohexyl-L-tyrosyl-3,5-dimethyl-L-tyrosyl-N-[(R)-1-(2-naphthyl)ethyl]-L-argininamide The compound 111 (184 mg, 0.14 mmol) was reacted in accordance with the method for synthesizing the compound 7 to obtain N-α-6-guanidinohexyl-L-tyrosyl-3,5-dimethyl-L-tyrosyl-N-[(R)-1-(2-naphthyl)ethyl]-L-argininamide (compound 112; yield: 91.8 mg).

FAB MS [M+H]$^+$=823

EXAMPLE 27

N-α-6-Guanidinohexyl-3,5-dimethyl-L-tyrosyl-3,5-dimethyl-L-tyrosyl-N-[(R)-1-(2-naphthyl)ethyl]-L-argininamide Step 1

3,5-Dimethyl-L-tyrosyl-3,5-dimethyl-L-tyrosyl-N-[(R)-1-(2-naphthyl)ethyl]-N-ω-(2,2,5,7,8-pentamethylchroman-6-sulfonyl)-L-argininamide N-α-9-Fluorenylmethoxycarbonyl-3,5-dimethyl-L-tyrosine (96.2 mg, 0.22 mmol) and the compound 109 (175 mg, 0.22 mmol) were reacted in accordance with the method for synthesizing the compound 1 to obtain 3,5-dimethyl-L-tyrosyl-3,5-dimethyl-L-tyrosyl-N-[(R)-1-(2-naphthyl)ethyl]-N-ω-(2,2,5,7,8-pentamethylchroman-6-sulfonyl)-L-argininamide (compound 113; yield: 210 mg).

Step 2

N-α-[6-(2,3-di-tert-Butoxycarbonylguanidino)hexyl]-3,5-dimethyl-L-tyrosyl-3,5-dimethyl-L-tyrosyl-N-[(R)-1-(2-naphthyl)ethyl]-N-ω-(2,2,5,7,8-pentamethylchroman-6-sulfonyl)-L-argininamide A crude product of the compound 5 (108 mg, 0.30 mmol) and the compound 113 (210 mg, 0.22 mmol) were reacted in accordance with the method for synthesizing the compound 6 to obtain N-α-[6-(2,3-di-tert-butoxycarbonylguanidino)hexyl-3,5-dimethyl-L-tyrosyl-3,5-dimethyl-L-tyrosyl-N-[(R)-1-(2-naphthyl)ethyl]-N-ω-(2,2,5,7,8-pentamethylchroman-6-sulfonyl)-L-argininamide (compound 114; yield: 216 mg).

Step 3

N-α-6-Guanidinohexyl-3,5-dimethyl-L-tyrosyl-3,5-dimethyl-L-tyrosyl-N-[(R)-1-(2-naphthyl)ethyl]-L-argininamide The compound 114 (208 mg, 0.16 mmol) was reacted in accordance with the method for synthesizing the compound 7 to obtain N-α-6-guanidinohexyl-3,5-dimethyl-L-tyrosyl-3,5-dimethyl-L-tyrosyl-N-[(R)-1-(2-naphthyl)ethyl]-L-argininamide (compound 115; yield: 122 mg).

FAB MS [M+H]$^+$=851

Test Example 1

Nociceptin Receptor Binding Test

A cell membrane suspension obtained from a human nociceptin-expressing cell was adjusted at a membrane protein level of 5 to 10 μg/mL in a Tris buffer [50 mM Tris-HCl (pH 7.8), 5 mM MgCl$_2$, 1 mM EGTA, 0.1% BSA]. To this suspension, [$^3$H] nociceptin (diluted to the final concentration of 0.08 nM in the Tris buffer) and a test substance were added, and the mixture was incubated at 25° C. for 60 minutes. Using a cell harvester and a washing solution [50 mM Tris-HCl (pH 7.8), 4° C.], the membrane was recovered onto the GF/B filter which had been pretreated with 0.3% PEI, and washed further 4 times. The filter was transferred into a vial, to which a scintillator was added, and then the radioactivity was measured using a liquid scintillation counter. A non-specific binding was regarded as a binding in the presence of 10 μM nociceptin, and the difference between the total binding and the non-specific binding was regarded as the specific binding. Based on the % binding inhibition in the presence of a test substance, the IC$_{50}$ was obtained and employed together with the Kd value of the [$^3$H] nociceptin to calculate the Ki value of the test substance (mol/L; hereinafter referred to as N value).

The results are shown in Table 1.

Test Example 2

μReceptor Binding Test

A human μ receptor-expressing cell membrane preparation (Receptor Biology) was adjusted at the membrane protein level of 8.5 μg/mL in a Tris buffer [50 mM Tris-HCl (pH 7.8), 5 mM MgCl$_2$, 1 mM EGTA, 0.1% BSA]. To this suspension, [$^3$H] diprenorphine (diluted to the final concentration of 0.13 nM in the Tris buffer) and a test substance were added, and the mixture was incubated at 25° C. for 90 minutes. Using a cell harvester and a washing solution [50 mM Tris-HCl (pH 7.8), 4° C.], the membrane was recovered onto the GF/B filter which had been pretreated with 0.3% PEI, and washed further 4 times. The filter was transferred into a vial, to which a scintillator was added, and then the radioactivity was measured using a liquid scintillation counter. A non-specific binding was regarded as a binding in the presence of 100 μM naloxone, and the difference between the total binding and the non-specific binding was regarded as the specific binding. Based on the % binding inhibition in the presence of a test substance, the IC$_{50}$ was obtained and employed together with the Kd value of the [$^3$H] diprenorphine to calculate the Ki value of the test substance (mol/L; hereinafter referred to as M value). The M value was divided by the N value obtained in Test Example 1 to judge the selectivity of the receptor binding of the test substance.

The results are shown in Table 1.

TABLE 1

Results of μ nociceptin receptor and receptor binding test

| Test compound (Example No.) | Ki for nociceptin receptor (N value) | Ki for μ receptor (M value) | Selectivity (M value/ N value) |
|---|---|---|---|
| 1 | $4.3 \times 10^{-10}$ (mol/L) | $4.0 \times 10^{-8}$ (mol/L) | 93 |
| 23 | $1.8 \times 10^{-9}$ (mol/L) | $5.9 \times 10^{-8}$ (mol/L) | 32 |
| 25 | $9.0 \times 10^{-10}$ (mol/L) | $1.4 \times 10^{-8}$ (mol/L) | 15 |
| 27 | $6.0 \times 10^{-10}$ (mol/L) | $1.0 \times 10^{-8}$ (mol/L) | 17 |

Based on the results shown in Table 1, each compound of the present invention was proven to be capable of binding the human nociceptin receptor.

Test Example 3

Mouse Formalin Test

Male mice (ddY; 4 to 5 weeks old) were kept at a room temperature of 21 to 25° C. and a humidity of 45 to 65% in a cage having a 12-hour light/12-hour dark cycle while being fed with feed and water ad libitum, whereby being acclimatized for a period of 1 week or longer. 6 Animals in each group were employed.

The compound of Example 1 was dissolved in physiological saline. Each mouse was placed in a cylindrical tube whose diameter was about 4 cm, immobilized at its tail, and a 27G needle connected to a 1 mL syringe was inserted into its tail vein, via which 0.1 mL/10 g body weight of the drug solution was administered rapidly. In a control group, physiological saline was administered. After administration, an absorbent cotton was used for hemostasis, and the animal was returned to the observation cage. The dose of the compound of Example 1 was 1 mg or 3 mg per 1 kg body weight of each mouse.

Subsequently, each mouse was acclimatized sufficiently to the observation cage, and then placed in a retainer for the drug administration. 20 μL of a 1% formalin solution was subcutaneously administered into the plantar region of the hindpaw, and the mouse was returned to the observation cage, and examined for the duration of any aversive behavior such as licking or biting the administered hindpaw extremity over a period of 30 minutes using a stopwatch.

The results are shown in Table 2.

TABLE 2

Results of formalin test

| Time after formalin administration (min) | Duration of aversive behavior (sec) | | |
|---|---|---|---|
| | Control | 1 mg/kg Group | 3 mg/kg Group |
| 0 to 10 | 128.3 (13.1) | 80.8** (9.3) | 41.00** (7.4) |
| 10 to 30 | 261.0 (31.7) | 163.8 (37.8) | 112.8** (16.5) |

Figure in ( ) represents a standard error.
**$P < 0.01$ compared with control by Dunnett's multiple comparison Based on the results of the tests described above, each inventive compound was proven to be capable of binding a human nociceptin receptor cell selectively, and to have an analgesic effect.

INDUSTRIAL APPLICABILITY

A compound according to the present invention is a nociceptin receptor (ORL-1) agonist and useful as an analgesic or anxiolytic agent.

The invention claimed is:

1. A compound of formula (1) or a pharmaceutically acceptable salt thereof:

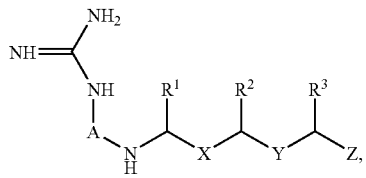

(1)

in which A is alkylene, formula (2) or formula (3):

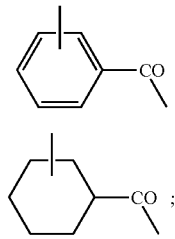

(2)

(3)

X and Y are the same or different and each represents —CONH— or —CH$_2$NH—;

R$^1$, R$^2$ and R$^3$ are the same or different and each represents alkyl, aryl or heteroaryl, wherein said alkyl aryl and heteroaryl are optionally substituted by 1 to 3 same or different substituents selected from the group consisting of halogen, nitro, hydroxy, cyano, carbamoyl, alkyl, aryl optionally substituted by hydroxy, heteroaryl optionally substituted by hydroxy, alkenyl, alkynyl, alkoxylcarbonyl, acyl, amino, monoalkylamino, dialkylamino, alkoxy, aryloxy, arylalkyloxy, alkylthio, arylalkylthio, heteroarylalkylthio, arylsulfonyl, alkylsulfonyl and guanidino; and Z represents —CON(R$^4$)R$^5$ or —CH$_2$N(R$^4$)R$^5$ wherein R$^4$ and R$^5$ are the same or different and each represents hydrogen, alkyl, aryl or heteroaryl, wherein said alkyl, aryl and heteroaryl are optionally substituted by 1 to 3 same or different substituents selected from the group consisting of halogen, nitro, hydroxy, carboxy, cyano, carbamoyl, alkyl, aryl optionally substituted by hydroxy, heteroaryl optionally substituted by hydroxy, alkenyl, alkynyl, alkoxycarbonyl, acyl, amino, monoalkylamino, dialkylamino, alkoxy, aryloxy, arylalkyloxy, alkylthio, arylalkylthio, heteroarylalkylthio, arylsulfonyl, alkylsulfonyl, guanidino, N-monoalkylcarbamoyl, N,N-dialkylcarbamoyl and hydroxymethyl.

2. A compound of formula (1) or a pharmaceutically acceptable salt thereof:

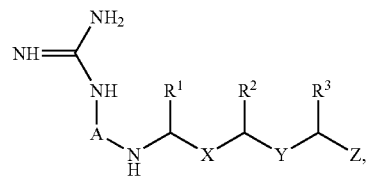

(1)

in which A is alkylene, formula (2) or formula (3):

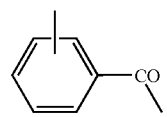

(2)

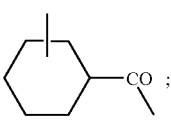

(3)

X and Y are the same or different and each represents —CONH— or —CH$_2$NH—;

Z represents —CON(R$^4$)R$^5$ or —CH$_2$N(R$^4$)R$^5$ wherein R$^4$ and R$^5$ are the same or different and each represents hydrogen, alkyl, aryl or heteroaryl, wherein said alkyl, aryl and heteroaryl are optionally substituted by 1 to 3 same or different substituents selected from the group consisting of halogen, nitro, hydroxy, carboxy, cyano, carbamoyl, alkyl, aryl optionally substituted by hydroxy, heteroaryl optionally substituted by hydroxy, alkenyl, alkynyl, alkoxycarbonyl, acyl, amino, monoalkylamino, dialkylamino, alkoxy, aryloxy, arylalkyloxy, alkylthio, arylalkylthio, heteroarylalkylthio, arylsulfonyl, alkylsulfonyl, guanidino, N-monoalkylcarbamoyl, N,N-dialkylcarbamoyl and hydroxymethyl;

R$^1$ is optionally substituted benzyl or naphthylmethyl; R$^2$ is 4-hydroxybenzyl; and R$^3$ is 4-aminobutyl or 3-guanidinopropyl.

3. A compound of formula (1) or pharmaceutically acceptable salt thereof according to claim 1, wherein:

A is pentamethylene, hexamethylene or heptamethylene;

R$^1$ is optionally substituted benzyl or naphthylmethyl;

R$^2$ is 4-hydroxybenzyl;

R$^3$ is 4-aminobutyl or 3 guanidinopropyl; and

Z is —CONH—CH(R$^6$)R$^7$, in which R$^6$ represents aryl or arylalkyl and R$^7$ represents hydrogen, carboxy, carbamoyl, hydroxymethyl or aryl.

4. A pharmaceutical composition having as an active ingredient a compound of formula (1) or pharmaceutically acceptable salt thereof according to any one of claims 1, 2 or 3.

5. A nociceptin receptor agonist composition having as an active ingredient a compound of formula (1) or a pharmaceutically acceptable salt thereof according to any one of claims 1, 2 or 3.

* * * * *

UNITED STATES PATENT AND TRADEMARK OFFICE
CERTIFICATE OF CORRECTION

PATENT NO.       : 7,163,921 B1
APPLICATION NO.  : 10/257238
DATED            : January 16, 2007
INVENTOR(S)      : Ishiyama et al.

It is certified that error appears in the above-identified patent and that said Letters Patent is hereby corrected as shown below:

In the Abstract at the first page of the patent, in the line after the structure of formula (1), delete the first "("; and after the "—" and before the "$CH_2)_nCO$—" please insert the parenthesis --(--

Signed and Sealed this

Eighth Day of May, 2007

JON W. DUDAS
*Director of the United States Patent and Trademark Office*